Figure 1:
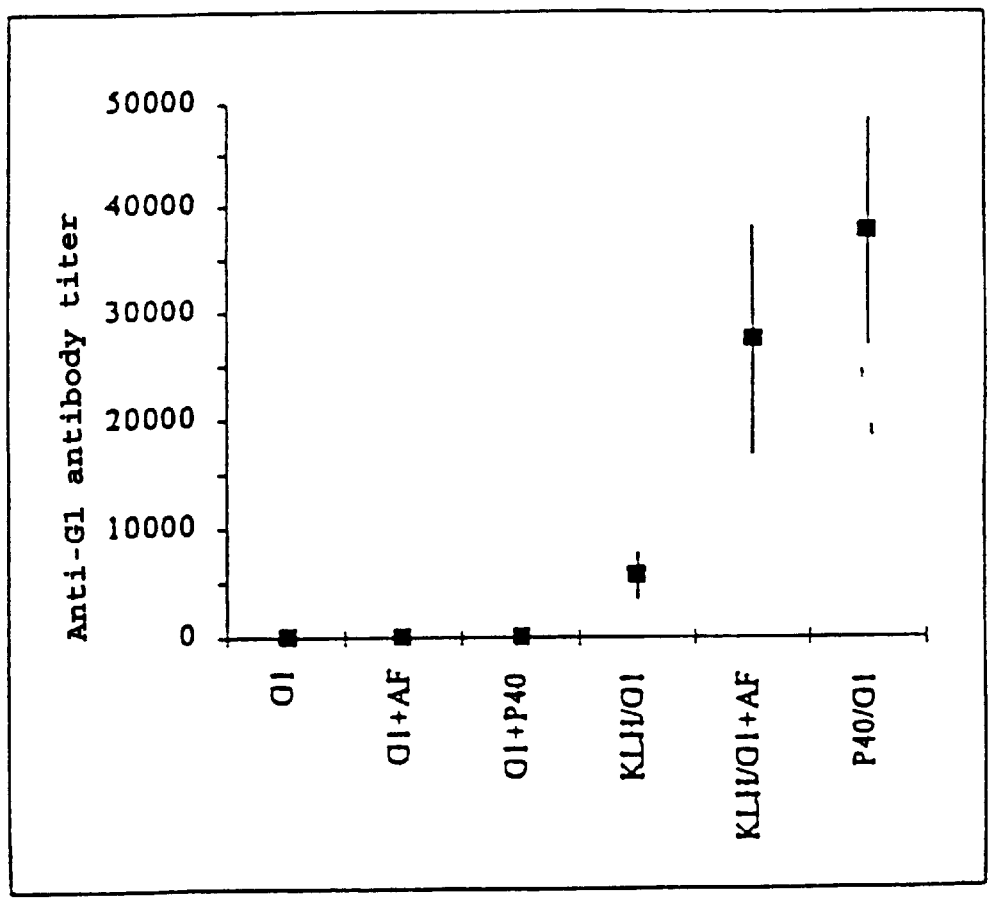

United States Patent [19]
Binz et al.

[11] Patent Number: 6,113,911
[45] Date of Patent: Sep. 5, 2000

[54] PEPTIDE FRAGMENT OF RESPIRATORY SYNCYTIAL VIRUS PROTEIN G, IMMUNOGENIC AGENT, PHARMACEUTICAL COMPOSITION CONTAINING IT AND PREPARATION METHOD

[75] Inventors: Hans Binz, Beaumont; Thien N'Guyen Ngoc, Saint-Julien-en-Genevois; Thierry Baussant, Bellegarde, all of France; Michel Trudel, Quebec, Canada

[73] Assignee: Pierre Fabre Medicament, Boulogne, France

[21] Appl. No.: 08/721,979

[22] PCT Filed: Apr. 6, 1995

[86] PCT No.: PCT/FR95/00444

§ 371 Date: Oct. 4, 1996

§ 102(e) Date: Oct. 4, 1996

[87] PCT Pub. No.: WO95/27787

PCT Pub. Date: Oct. 19, 1995

[30] Foreign Application Priority Data

Apr. 6, 1994 [FR] France ................................ 94 04009

[51] Int. Cl.[7] ........................ A61K 39/155; A61K 39/12
[52] U.S. Cl. .................................... 424/211.1; 424/204.1; 424/184.1; 424/185.1; 424/186.1; 435/69.1; 435/69.3; 536/23.72
[58] Field of Search ............................. 424/211.1, 204.1, 424/184.1, 185.1, 186.1; 435/69.1, 69.3; 536/23.72

[56] References Cited

FOREIGN PATENT DOCUMENTS

| 0 355 737 | 2/1990 | European Pat. Off. . |
|---|---|---|
| 89 05823 | 6/1989 | WIPO . |
| 92 04375 | 3/1992 | WIPO . |
| 92 20805 | 11/1992 | WIPO . |
| 93 14207 | 7/1993 | WIPO . |

OTHER PUBLICATIONS

Trudel, M., E.J. Stott, G. Taylor, D. Oth, G. Mercier, F. Nadon, C. Seguin, C. Simard, and M. Lacroix, *Synthetic Peptides Corresponding to the F Protein of RSV Stimulate Murine B and T Cells but Fail to Confer Protection*, Arch Virol 117, pp. 59–71 (1991).

Garcia–Barreno, B., et al., "Marked Differences in the Antigenic Structure of Human Respiratory Syncytial Virus F and G Glycoproteins", Journal of Virology, 63(2) (1989) pp. 925–932.

Lawrence, J., et al., "Molecular and Evolutionary Relationships Among Enteric Bacteria", Journal of General Microbiology, 137(8) (1991) pp. 1911–1921.

Norrby, E., et al., "Site–Directed Serology with Synthetic Peptides Representing the Large Glycoprotein G of Respiratory Syncytial Virus", Proc. Natl. Acad. Sci. U.S.A., 84(18) (1987) pp. 6572–6576.

Counseil International de la Langue Grancaise Fondation Postuniversitaire Interculturelle, *Dictionnaire de Genetique*, p. 155 (1991)—With Translation.

Printout of Peptide Information From the International Search Authority in Europe.

Boswell et al, 1988, Oxford University Press, Computational Molecular Biology, pp. 161–178.

Akerlind–Stopner et al, Oct. 1990, J. of Virology, vol. 64, No. 10, pp. 5143–5148.

Trudel et al, 1991, Virology, vol. 185, p. 749–757).

Cane et al, 1991, J. of General Virlogy, vol. 72, pp. 2091–2096.

*Primary Examiner*—Ali Salimi
*Attorney, Agent, or Firm*—The firm of Gordon W. Hueschen

[57] ABSTRACT

A polypeptide useful as an immunogen element and characterized in that it is carried on the peptide sequence between amino acid residues 130–230 of the G protein sequence of the human respiratory syncytial virus of subgroups A and B, or of the bovine respiratory syncytial virus, or on a sequence at least 80% homologous thereto. An immunogenic agent or pharmaceutical composition containing said polypeptide, and methods for preparing and using the same, are also disclosed.

2 Claims, 4 Drawing Sheets

SEQUENCE LISTING (1) GENERAL INFORMATION:

(iii) NUMBER OF SEQUENCES: 75

(2) INFORMATION FOR SEQ ID NO: 1:

(i) SEQUENCE CHARACTERISTICS:
      (A) LENGTH: 303 base pairs
      (B) TYPE: nucleic acid
      (C) STRANDEDNESS: single
      (D) TOPOLOGY: linear (ii) MOLECULE TYPE: peptide (ix) FEATURE:
      (A) NAME/KEY: CDS
      (B) LOCATION:1..303
      (D) OTHER INFORMATION:/product= "G2A"
          /note= "sequence 130-230"

(xi) SEQUENCE DESCRIPTION: SEQ ID NO: 1:

```
ACC GTG AAA ACC AAA AAC ACC ACG ACC ACC CAG ACC CAG CCG AGC AAA       48
Thr Val Lys Thr Lys Asn Thr Thr Thr Thr Gln Thr Gln Pro Ser Lys
 1               5                  10                  15

CCG ACC ACC AAA CAG CGT CAG AAC AAA CCG CCG AAC AAA CCG AAC AAC       96
Pro Thr Thr Lys Gln Arg Gln Asn Lys Pro Pro Asn Lys Pro Asn Asn
                20                  25                  30

GAT TTC CAT TTC GAA GTG TTC AAC TTC GTG CCG TGC AGC ATC TGC AGC      144
Asp Phe His Phe Glu Val Phe Asn Phe Val Pro Cys Ser Ile Cys Ser
            35                  40                  45

AAC AAC CCG ACC TGC TGG GCG ATC TGC AAA CGT ATC CCG AAC AAA AAA      192
Asn Asn Pro Thr Cys Trp Ala Ile Cys Lys Arg Ile Pro Asn Lys Lys
        50                  55                  60

CCG GGC AAA AAA ACC ACG ACC AAA CCG ACC AAA AAA CCG ACC TTC AAA      240
Pro Gly Lys Lys Thr Thr Thr Lys Pro Thr Lys Lys Pro Thr Phe Lys
65                  70                  75                  80

ACC ACC AAA AAA GAT CAT AAA CCG CAG ACC ACC AAA CCG AAA GAA GTG      288
Thr Thr Lys Lys Asp His Lys Pro Gln Thr Thr Lys Pro Lys Glu Val
                85                  90                  95

CCG ACC ACC AAA CCG                                                  303
Pro Thr Thr Lys Pro
               100
```

(2) INFORMATION FOR SEQ ID NO: 2:

(i) SEQUENCE CHARACTERISTICS:
    (A) LENGTH: 303 base pairs
    (B) TYPE: nucleic acid
    (C) STRANDEDNESS: single
    (D) TOPOLOGY: linear (ii) MOLECULE TYPE: peptide (ix) FEATURE:
    (A) NAME/KEY: CDS
    (B) LOCATION:1..303
    (D) OTHER INFORMATION:/product= "G2B"
        /note= "sequence 130-230"

(xi) SEQUENCE DESCRIPTION: SEQ ID NO: 2:

```
ACC GCG CAG ACC AAA GGC CGT ATC ACC ACC AGC ACC CAG ACC AAC AAA      48
Thr Ala Gln Thr Lys Gly Arg Ile Thr Thr Ser Thr Gln Thr Asn Lys
 1               5                  10                  15

CCG AGC ACC AAA AGC CGT AGC AAA AAC CCG CCG AAA AAA CCG AAA GAT      96
Pro Ser Thr Lys Ser Arg Ser Lys Asn Pro Pro Lys Lys Pro Lys Asp
                20                  25                  30

GAT TAC CAC TTC GAA GTG TTC AAC TTC GTG CCC TGC AGC ATC TGC GGC     144
Asp Tyr His Phe Glu Val Phe Asn Phe Val Pro Cys Ser Ile Cys Gly
             35                  40                  45

AAC AAC CAG CTG TGC AAA AGC ATC TGC AAA ACC ATC CCG AGC AAC AAA     192
Asn Asn Gln Leu Cys Lys Ser Ile Cys Lys Thr Ile Pro Ser Asn Lys
 50                  55                  60

CCG AAA AAG AAA CCG ACC ATC AAA CCG ACC AAC AAA CCG ACC ACC AAA     240
Pro Lys Lys Lys Pro Thr Ile Lys Pro Thr Asn Lys Pro Thr Thr Lys
 65                  70                  75                  80

ACC ACC AAC AAA CGT GAT CCG AAA ACC CCG GCG AAA ATG CCG AAG AAG     288
Thr Thr Asn Lys Arg Asp Pro Lys Thr Pro Ala Lys Met Pro Lys Lys
                 85                  90                  95

GAA ATC ATC ACC AAC                                                 303
Glu Ile Ile Thr Asn
            100
```

(2) INFORMATION FOR SEQ ID NO: 3:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..303
        (D) OTHER INFORMATION:/product= "G2AdeltaCys"
            /note= "sequence 130-230"

(xi) SEQUENCE DESCRIPTION: SEQ ID NO: 3:

```
ACC GTG AAA ACC AAA AAC ACC ACG ACC ACC CAG ACC CAG CCG AGC AAA      48
Thr Val Lys Thr Lys Asn Thr Thr Thr Thr Gln Thr Gln Pro Ser Lys
 1               5                  10                  15

CCG ACC ACC AAA CAG CGT CAG AAC AAA CCG CCG AAC AAA CCG AAC AAC      96
Pro Thr Thr Lys Gln Arg Gln Asn Lys Pro Pro Asn Lys Pro Asn Asn
                20                  25                  30

GAT TTC CAT TTC GAA GTG TTC AAC TTC GTG CCG AGC AGC ATC TGC AGC     144
Asp Phe His Phe Glu Val Phe Asn Phe Val Pro Ser Ser Ile Cys Ser
             35                  40                  45

AAC AAC CCG ACC TGC TGG GCG ATC AGC AAA CGT ATC CCG AAC AAA AAA     192
Asn Asn Pro Thr Cys Trp Ala Ile Ser Lys Arg Ile Pro Asn Lys Lys
 50                  55                  60
```

```
CCG GGC AAA AAA ACC ACG ACC AAA CCG ACC AAA AAA CCG ACC TTC AAA       240
Pro Gly Lys Lys Thr Thr Thr Lys Pro Thr Lys Lys Pro Thr Phe Lys
 65              70                  75                  80

ACC ACC AAA AAA GAT CAT AAA CCG CAG ACC ACC AAA CCG AAA GAA GTG       288
Thr Thr Lys Lys Asp His Lys Pro Gln Thr Thr Lys Pro Lys Glu Val
                 85                  90                  95

CCG ACC ACC AAA CCG                                                   303
Pro Thr Thr Lys Pro
            100
```

(2) INFORMATION FOR SEQ ID NO: 4:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..303
        (D) OTHER INFORMATION:/product= "G2BdeltaCys"
            /note= "sequence 130-230"

(xi) SEQUENCE DESCRIPTION: SEQ ID NO: 4:

```
ACC GCG CAG ACC AAA GGC CGT ATC ACC ACC AGC ACC CAG ACC AAC AAA        48
Thr Ala Gln Thr Lys Gly Arg Ile Thr Thr Ser Thr Gln Thr Asn Lys
  1               5                  10                  15

CCG AGC ACC AAA AGC CGT AGC AAA AAC CCG CCG AAA AAA CCG AAA GAT        96
Pro Ser Thr Lys Ser Arg Ser Lys Asn Pro Pro Lys Lys Pro Lys Asp
                 20                  25                  30

GAT TAC CAC TTC GAA GTG TTC AAC TTC GTG CCC AGC AGC ATC TGC GGC       144
Asp Tyr His Phe Glu Val Phe Asn Phe Val Pro Ser Ser Ile Cys Gly
                 35                  40                  45

AAC AAC CAG CTG TGC AAA AGC ATC AGC AAA ACC ATC CCG AGC AAC AAA       192
Asn Asn Gln Leu Cys Lys Ser Ile Ser Lys Thr Ile Pro Ser Asn Lys
             50                  55                  60

CCG AAA AAG AAA CCG ACC ATC AAA CCG ACC AAC AAA CCG ACC ACC AAA       240
Pro Lys Lys Lys Pro Thr Ile Lys Pro Thr Asn Lys Pro Thr Thr Lys
 65              70                  75                  80

ACC ACC AAC AAA CGT GAT CCG AAA ACC CCG GCG AAA ATG CCG AAG AAG       288
Thr Thr Asn Lys Arg Asp Pro Lys Thr Pro Ala Lys Met Pro Lys Lys
                 85                  90                  95

GAA ATC ATC ACC AAC                                                   303
Glu Ile Ile Thr Asn
            100
```

(2) INFORMATION FOR SEQ ID NO: 5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..42
        (D) OTHER INFORMATION:/note= "sequence 174-187 / name :
            G1ACys"

(xi) SEQUENCE DESCRIPTION: SEQ ID NO: 5:

```
AGC ATC TGC AGC AAC AAC CCG ACC TGC TGG GCG ATC TGC AAA          42
Ser Ile Cys Ser Asn Asn Pro Thr Cys Trp Ala Ile Cys Lys
 1               5                  10
```

(2) INFORMATION FOR SEQ ID NO: 6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..42
        (D) OTHER INFORMATION:/note= "sequence 174-187 / name
            G1BCys"

(xi) SEQUENCE DESCRIPTION: SEQ ID NO: 6:

```
AGC ATC TGC GGC AAC AAC CAG CTG TGC AAA AGC ATC TGC AAA          42
Ser Ile Cys Gly Asn Asn Gln Leu Cys Lys Ser Ile Cys Lys
 1               5                  10
```

(2) INFORMATION FOR SEQ ID NO: 7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..42
        (D) OTHER INFORMATION:/note= "sequence 174-187 / name :
            G1A"

(xi) SEQUENCE DESCRIPTION: SEQ ID NO: 7:

```
AGC ATC TGC AGC AAC AAC CCG ACC TGC TGG GCG ATC AGC AAA          42
Ser Ile Cys Ser Asn Asn Pro Thr Cys Trp Ala Ile Ser Lys
 1               5                  10
```

(2) INFORMATION FOR SEQ ID NO: 8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..42
        (D) OTHER INFORMATION:/note= "sequence 174-187 / name :
            G1B"

(xi) SEQUENCE DESCRIPTION: SEQ ID NO: 8:

```
AGC ATC TGC GGC AAC AAC CAG CTG TGC AAA AGC ATC AGC AAA          42
Ser Ile Cys Gly Asn Asn Gln Leu Cys Lys Ser Ile Ser Lys
 1               5                  10
```

(2) INFORMATION FOR SEQ ID NO: 9:

(i) SEQUENCE CHARACTERISTICS:
        (A) LENGTH: 14 amino acids
        (B) TYPE: amino acid (C) STRANDEDNESS: single
        (D) TOPOLOGY: linear (ii) MOLECULE TYPE: peptide (ix) FEATURE:
        (A) NAME/KEY: Modified-site
        (B) LOCATION:9
        (D) OTHER INFORMATION:/product= "Orn"
            /note= "sequence 174-187 / name : G1'A"

(xi) SEQUENCE DESCRIPTION: SEQ ID NO: 9:

Ser Ile Asp Ser Asn Asn Pro Thr Xaa Trp Ala Ile Cys Lys
1               5                   10

(2) INFORMATION FOR SEQ ID NO: 10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:9
        (D) OTHER INFORMATION:/product= "Orn"
            /note= "sequence 174-187 / name : G1'B"

(xi) SEQUENCE DESCRIPTION: SEQ ID NO: 10:

Ser Ile Asp Gly Asn Asn Gln Leu Xaa Lys Ser Ile Cys Lys
1               5                   10

(2) INFORMATION FOR SEQ ID NO: 11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:9
        (D) OTHER INFORMATION:/product= "Orn"
            /note= "sequence 174-187 / name : G1'AdeltaC"

(xi) SEQUENCE DESCRIPTION: SEQ ID NO: 11:

Ser Ile Asp Ser Asn Asn Pro Thr Xaa Trp Ala Ile Ser Lys
1               5                   10

(2) INFORMATION FOR SEQ ID NO: 12:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:9
        (D) OTHER INFORMATION:/product= "Orn"
            /note= "sequence 174-187 / name : G1'BdeltaC"

(xi) SEQUENCE DESCRIPTION: SEQ ID NO: 12:

```
Ser Ile Asp Gly Asn Asn Gln Leu Xaa Lys Ser Ile Ser Lys
 1               5                  10
```

(2) INFORMATION FOR SEQ ID NO: 13:

(i) SEQUENCE CHARACTERISTICS:
        (A) LENGTH: 1008 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..1008
        (D) OTHER INFORMATION:/note= "name : P40"

(xi) SEQUENCE DESCRIPTION: SEQ ID NO: 13:

```
GCT CCG AAA GAT AAC ACC TGG TAT GCA GGT GGT AAA CTG GGT TGG TCC        48
Ala Pro Lys Asp Asn Thr Trp Tyr Ala Gly Gly Lys Leu Gly Trp Ser
 1               5                  10                  15

CAG TAT CAC GAC ACC GGT TTC TAC GGT AAC GGT TTC CAG AAC AAC AAC        96
Gln Tyr His Asp Thr Gly Phe Tyr Gly Asn Gly Phe Gln Asn Asn Asn
                 20                  25                  35

GGT CCG ACC CGT AAC GAT CAG CTT GGT GCT GGT GCG TTC GGT GGT TAC       144
Gly Pro Thr Arg Asn Asp Gln Leu Gly Ala Gly Ala Phe Gly Gly Tyr
                 40                  45                  50

CAG GTT AAC CCG TAC CTC GGT TTC GAA ATG GGT TAT GAC TGG CTG GGC       192
Gln Val Asn Pro Tyr Leu Gly Phe Glu Met Gly Tyr Asp Trp Leu Gly
             55                  60                  65

CGT ATG GCA TAT AAA GGC AGC GTT GAC AAC GGT GCT TTC AAA GCT CAG       240
Arg Met Ala Tyr Lys Gly Ser Val Asp Asn Gly Ala Phe Lys Ala Gln
     70                  80                  85

GGC GTT CAG CTG ACC GCT AAA CTG GGT TAC CCG ATC ACT GAC GAT CTG       288
Gly Val Gln Leu Thr Ala Lys Leu Gly Tyr Pro Ile Thr Asp Asp Leu
 90                  95                  100                 105

GAC ATC TAC ACC CGT CTG GGC GGC ATG GTT TGG CGC GCT GAC TCC AAA       336
Asp Ile Tyr Thr Arg Leu Gly Gly Met Val Trp Arg Ala Asp Ser Lys
                 110                 115                 120

GGC AAC TAC GCT TCT ACC GGC GTT TCC CGT AGC GAA CAC GAC ACT GGC       384
Gly Asn Tyr Ala Ser Thr Gly Val Ser Arg Ser Glu His Asp Thr Gly
                 125                 130                 135

GTT TCC CCA GTA TTT GCT GGC GGC GTA GAG TGG GCT GTT ACT CGT GAC       432
Val Ser Pro Val Phe Ala Gly Gly Val Glu Trp Ala Val Thr Arg Asp
             140                 145                 150

ATC GCT ACC CGT CTG GAA TAC CAG TGG GTT AAC AAC ATC GGC GAC GCG       480
Ile Ala Thr Arg Leu Glu Tyr Gln Trp Val Asn Asn Ile Gly Asp Ala
     155                 160                 165

GGC ACT GTG GGT ACC CGT CCT GAT AAC GGC ATG CTG AGC CTG GGC GTT       528
Gly Thr Val Gly Thr Arg Pro Asp Asn Gly Met Leu Ser Leu Gly Val
170                 175                 180                 185

TCC TAC CGC TTC GGT CAG GAA GAT GCT GCA CCG GTT GTT GCT CCG GCT       576
Ser Tyr Arg Phe Gly Gln Glu Asp Ala Ala Pro Val Val Ala Pro Ala
                 190                 195                 200

CCG GCT CCG GCT CCG GAA GTG GCT ACC AAG CAC TTC ACC CTG AAG TCT       624
Pro Ala Pro Ala Pro Glu Val Ala Thr Lys His Phe Thr Leu Lys Ser
                 205                 210                 215

GAC GTT CTG TTC AAC TTC AAC AAA GCT ACC CTG AAA CCG GAA GGT CAG       672
Asp Val Leu Phe Asn Phe Asn Lys Ala Thr Leu Lys Pro Glu Gly Gln
                 220                 225                 230

CAG GCT CTG GAT CAG CTG TAC ACT CAG CTG AGC AAC ATG GAT CCG AAA       720
Gln Ala Leu Asp Gln Leu Tyr Thr Gln Leu Ser Asn Met Asp Pro Lys
```

```
                235                 245                 250
GAC GGT TCC GCT GTT GTT CTG GGC TAC ACC GAC CGC ATC GGT TCC GAA      768
Asp Gly Ser Ala Val Val Leu Gly Tyr Thr Asp Arg Ile Gly Ser Glu
255                 260                 265                 270

GCT TAC AAC CAG CAG CTG TCT GAG AAA CGT GCT CAG TCC GTT GTT GAC      816
Ala Tyr Asn Gln Gln Leu Ser Glu Lys Arg Ala Gln Ser Val Val Asp
                275                 280                 285

TAC CTG GTT GCT AAA GGC ATC CCG GCT GGC AAA ATC TCC GCT CGC GGC      864
Tyr Leu Val Ala Lys Gly Ile Pro Ala Gly Lys Ile Ser Ala Arg Gly
                290                 295                 300

ATG GGT GAA TCC AAC CCG GTT ACT GGC AAC ACC TGT GAC AAC GTG AAA      912
Met Gly Glu Ser Asn Pro Val Thr Gly Asn Thr Cys Asp Asn Val Lys
                305                 310                 315

GCT CGC GCT GCC CTG ATC GAT TGC CTG GCT CCG GAT CGT CGT GTA GAG      960
Ala Arg Ala Ala Leu Ile Asp Cys Leu Ala Pro Asp Arg Arg Val Glu
320                 325                 330

ATC GAA GTT AAA GGC TAC AAA GAA GTT GTA ACT CAG CCG GCG GGT TAA     1008
Ile Glu Val Lys Gly Tyr Lys Glu Val Val Thr Gln Pro Ala Gly
335                 340                 345                 350

(2) INFORMATION FOR SEQ ID NO: 14:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..303
        (D) OTHER INFORMATION:/note= "sequence 130-230 / name
            G2AdeltaCF"

(xi) SEQUENCE DESCRIPTION: SEQ ID NO: 14:

ACC GTG AAA ACC AAA AAC ACC ACG ACC ACC CAG ACC CAG CCG AGC AAA       48
Thr Val Lys Thr Lys Asn Thr Thr Thr Thr Gln Thr Gln Pro Ser Lys
1                 5                  10                  15

CCG ACC ACC AAA CAG CGT CAG AAC AAA CCG CCG AAC AAA CCG AAC AAC       96
Pro Thr Thr Lys Gln Arg Gln Asn Lys Pro Pro Asn Lys Pro Asn Asn
                20                  25                  30

GAT TCC CAT TCC GAA GTG TCC AAC TCC GTG CCG AGC AGC ATC TGC AGC      144
Asp Ser His Ser Glu Val Ser Asn Ser Val Pro Ser Ser Ile Cys Ser
                35                  40                  45

AAC AAC CCG ACC TGC TGG GCG ATC AGC AAA CGT ATC CCG AAC AAA AAA      192
Asn Asn Pro Thr Cys Trp Ala Ile Ser Lys Arg Ile Pro Asn Lys Lys
50                  55                  60

CCG GGC AAA AAA ACC ACG ACC AAA CCG ACC AAA AAA CCG ACC TTC AAA      240
Pro Gly Lys Lys Thr Thr Thr Lys Pro Thr Lys Lys Pro Thr Phe Lys
65                  70                  75                  80

ACC ACC AAA AAA GAT CAT AAA CCG CAG ACC ACC AAA CCG AAA GAA GTG      288
Thr Thr Lys Lys Asp His Lys Pro Gln Thr Thr Lys Pro Lys Glu Val
                85                  90                  95

CCG ACC ACC AAA CCG                                                  303
Pro Thr Thr Lys Pro
                100

(2) INFORMATION FOR SEQ ID NO: 15:

(i) SEQUENCE CHARACTERISTICS:
        (A) LENGTH: 51 base pairs
        (B) TYPE: nucleic acid
```

(C) STRANDEDNESS: single
        (D) TOPOLOGY: linear (ii) MOLECULE TYPE: peptide (ix) FEATURE:
        (A) NAME/KEY: CDS
        (B) LOCATION:1..51
        (D) OTHER INFORMATION:/note= "sequence 171-187 / name :
            G4A"

(xi) SEQUENCE DESCRIPTION: SEQ ID NO: 15:

```
GTG CCG TGC AGC ATC TGC AGC AAC AAC CCG ACC TGC TGG GCG ATC TGC        48
Val Pro Cys Ser Ile Cys Ser Asn Asn Pro Thr Cys Trp Ala Ile Cys
 1               5                  10                  15

AAA                                                                    51
Lys
```

(2) INFORMATION FOR SEQ ID NO: 16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..51
        (D) OTHER INFORMATION:/note= "sequence 171-187 / name :
            G4AdeltaC"

(xi) SEQUENCE DESCRIPTION: SEQ ID NO: 16:

```
GTG CCG AGC AGC ATC TGC AGC AAC AAC CCG ACC TGC TGG GCG ATC AGC        48
Val Pro Ser Ser Ile Cys Ser Asn Asn Pro Thr Cys Trp Ala Ile Ser
 1               5                  10                  15

AAA                                                                    51
Lys
```

(2) INFORMATION FOR SEQ ID NO: 17:

(i) SEQUENCE CHARACTERISTICS:
        (A) LENGTH: 51 base pairs
        (B) TYPE: nucleic acid
        (C) STRANDEDNESS: single
        (D) TOPOLOGY: linear
    (ii) MOLECULE TYPE: peptide (ix) FEATURE:
        (A) NAME/KEY: CDS
        (B) LOCATION:1..51
        (D) OTHER INFORMATION:/note= "sequence 171-187 / name :
            G4B"

(xi) SEQUENCE DESCRIPTION: SEQ ID NO: 17:

```
GTG CCC TGC AGC ATC TGC GGC AAC AAC CAG CTG TGC AAA AGC ATC TGC        48
Val Pro Cys Ser Ile Cys Gly Asn Asn Gln Leu Cys Lys Ser Ile Cys
 1               5                  10                  15

AAA                                                                    51
Lys
```

(2) INFORMATION FOR SEQ ID NO: 18:
    (i) SEQUENCE CHARACTERISTICS:
        (A) LENGTH: 51 base pairs
        (B) TYPE: nucleic acid
        (C) STRANDEDNESS: single
        (D) TOPOLOGY: linear

```
        (ii) MOLECULE TYPE: peptide (ix) FEATURE:
             (A) NAME/KEY: CDS
             (B) LOCATION:1..51
             (D) OTHER INFORMATION:/note= "sequence 171-187 / name :
                 G4BdeltaC"

(xi) SEQUENCE DESCRIPTION: SEQ ID NO: 18:

GTG CCC AGC AGC ATC TGC GGC AAC AAC CAG CTG TGC AAA AGC ATC AGC       48
Val Pro Ser Ser Ile Cys Gly Asn Asn Gln Leu Cys Lys Ser Ile Ser
 1               5                  10                  15

AAA                                                                    51
Lys (2) INFORMATION FOR SEQ ID NO: 19:

(i) SEQUENCE CHARACTERISTICS:
             (A) LENGTH: 17 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Modified-site
             (B) LOCATION:12
             (D) OTHER INFORMATION:/product= "Orn"

(ix) FEATURE:
             (A) NAME/KEY: Modified-site
             (B) LOCATION:16
             (D) OTHER INFORMATION:/product= "Orn"
                 /note= "sequence 171-187 / name : G4'A"

(xi) SEQUENCE DESCRIPTION: SEQ ID NO: 19:

Val Pro Asp Ser Ile Asp Ser Asn Asn Pro Thr Xaa Trp Ala Ile Xaa
 1               5                  10                  15

Lys (2) INFORMATION FOR SEQ ID NO: 20:

(i) SEQUENCE CHARACTERISTICS:
             (A) LENGTH: 17 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Modified-site
             (B) LOCATION:12
             (D) OTHER INFORMATION:/product= "Orn"
                 /note= "sequence 171-187 / name : G4'AdeltaC"

(xi) SEQUENCE DESCRIPTION: SEQ ID NO: 20:

Val Pro Ser Ser Ile Asp Ser Asn Asn Pro Thr Xaa Trp Ala Ile Ser
 1               5                  10                  15

Lys (2) INFORMATION FOR SEQ ID NO: 21:

(i) SEQUENCE CHARACTERISTICS:
             (A) LENGTH: 17 amino acids
             (B) TYPE: amino acid
             (C) STRANDEDNESS: single
             (D) TOPOLOGY: linear
```

(ii) MOLECULE TYPE: peptide (ix) FEATURE:
    (A) NAME/KEY: Peptide
    (B) LOCATION:12
    (D) OTHER INFORMATION:/product= "Orn"

(ix) FEATURE:
    (A) NAME/KEY: Peptide
    (B) LOCATION:16
    (D) OTHER INFORMATION:/product= "Orn"

(xi) SEQUENCE DESCRIPTION: SEQ ID NO: 21:

```
Val Pro Asp Ser Ile Asp Gly Asn Asn Gln Leu Xaa Lys Ser Ile Xaa
1               5                   10                  15

Lys
```

(2) INFORMATION FOR SEQ ID NO: 22:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:12
        (D) OTHER INFORMATION:/product= "Orn"

(xi) SEQUENCE DESCRIPTION: SEQ ID NO: 22:

```
Val Pro Ser Ser Ile Asp Gly Asn Asn Gln Leu Xaa Lys Ser Ile Ser
1               5                   10                  15

Lys
```

(2) INFORMATION FOR SEQ ID NO: 23:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..183
        (D) OTHER INFORMATION:/product= "G200A"
            /note= "sequence 140-200"

(xi) SEQUENCE DESCRIPTION: SEQ ID NO: 23:

```
CAG ACC CAG CCG AGC AAA CCG ACC ACC AAA CAG CGT CAG AAC AAA CCG      48
Gln Thr Gln Pro Ser Lys Pro Thr Thr Lys Gln Arg Gln Asn Lys Pro
1               5                   10                  15

CCG AAC AAA CCG AAC AAC GAT TTC CAT TTC GAA GTG TTC AAC TTC GTG      96
Pro Asn Lys Pro Asn Asn Asp Phe His Phe Glu Val Phe Asn Phe Val
                20                  25                  30

CCG TGC AGC ATC TGC AGC AAC AAC CCG ACC TGC TGG GCG ATC TGC AAA     144
Pro Cys Ser Ile Cys Ser Asn Asn Pro Thr Cys Trp Ala Ile Cys Lys
            35                  40                  45

CGT ATC CCG AAC AAA AAA CCG GGC AAA AAA ACC ACG ACC                 183
Arg Ile Pro Asn Lys Lys Pro Gly Lys Lys Thr Thr Thr
        50                  55                  60
```

(2) INFORMATION FOR SEQ ID NO: 24:

(i) SEQUENCE CHARACTERISTICS:
    (A) LENGTH: 177 base pairs
    (B) TYPE: nucleic acid
    (C) STRANDEDNESS: single
    (D) TOPOLOGY: linear (ii) MOLECULE TYPE: peptide (ix) FEATURE:
    (A) NAME/KEY: CDS
    (B) LOCATION:1..177
    (D) OTHER INFORMATION:/product= "G198A"
        /note= "sequence 140-198"

(xi) SEQUENCE DESCRIPTION: SEQ ID NO: 24:

```
CAG ACC CAG CCG AGC AAA CCG ACC ACC AAA CAG CGT CAG AAC AAA CCG     48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG     96
Pro Asn Lys Pro Asn Asn Asp Phe His Phe Glu Val Phe Asn Phe Val
                20                  25                  30

CCG TGC AGC ATC TGC AGC AAC AAC CCG ACC TGC TGG GCG ATC TGC AAA    144
Pro Cys Ser Ile Cys Ser Asn Asn Pro Thr Cys Trp Ala Ile Cys Lys
            35                  40                  45

CGT ATC CCG AAC AAA AAA CCG GGC AAA AAA ACC                        177
Arg Ile Pro Asn Lys Lys Pro Gly Lys Lys Thr
        50                  55
```

(2) INFORMATION FOR SEQ ID NO: 25:

(i) SEQUENCE CHARACTERISTICS:
    (A) LENGTH: 171 base pairs
    (B) TYPE: nucleic acid
    (C) STRANDEDNESS: single
    (D) TOPOLOGY: linear (ii) MOLECULE TYPE: peptide (ix) FEATURE:
    (A) NAME/KEY: CDS
    (B) LOCATION:1..171
    (D) OTHER INFORMATION:/product= "G196A"
        /note= "sequence 140-196"

(xi) SEQUENCE DESCRIPTION: SEQ ID NO: 25:

```
CAG ACC CAG CCG AGC AAA CCG ACC ACC AAA CAG CGT CAG AAC AAA CCG     48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG     96
Pro Asn Lys Pro Asn Asn Asp Phe His Phe Glu Val Phe Asn Phe Val
                20                  25                  30

CCG TGC AGC ATC TGC AGC AAC AAC CCG ACC TGC TGG GCG ATC TGC AAA    144
Pro Cys Ser Ile Cys Ser Asn Asn Pro Thr Cys Trp Ala Ile Cys Lys
            35                  40                  45

CGT ATC CCG AAC AAA AAA CCG GGC AAA                                171
Arg Ile Pro Asn Lys Lys Pro Gly Lys
        50                  55
```

(2) INFORMATION FOR SEQ ID NO: 26:

(i) SEQUENCE CHARACTERISTICS:
    (A) LENGTH: 165 base pairs
    (B) TYPE: nucleic acid
    (C) STRANDEDNESS: single
    (D) TOPOLOGY: linear (ii) MOLECULE TYPE: peptide (ix) FEATURE:
    (A) NAME/KEY: CDS
    (B) LOCATION:1..165
    (D) OTHER INFORMATION:/product= "G194A"
        /note= "sequence 140-194"

(xi) SEQUENCE DESCRIPTION: SEQ ID NO: 26:

```
CAG ACC CAG CCG AGC AAA CCG ACC ACC AAA CAG CGT CAG AAC AAA CCG         48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG         96
Pro Asn Lys Pro Asn Asn Asp Phe His Phe Glu Val Phe Asn Phe Val
             20                  25                  30

CCG TGC AGC ATC TGC AGC AAC AAC CCG ACC TGC TGG GCG ATC TGC AAA        144
Pro Cys Ser Ile Cys Ser Asn Asn Pro Thr Cys Trp Ala Ile Cys Lys
         35                  40                  45

CGT ATC CCG AAC AAA AAA CCG                                            165
Arg Ile Pro Asn Lys Lys Pro
         50              55
```

(2) INFORMATION FOR SEQ ID NO: 27:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..159
        (D) OTHER INFORMATION:/product= "G192A"
            /note= "sequence 140-192"

(xi) SEQUENCE DESCRIPTION: SEQ ID NO: 27:

```
CAG ACC CAG CCG AGC AAA CCG ACC ACC AAA CAG CGT CAG AAC AAA CCG         48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG         96
Pro Asn Lys Pro Asn Asn Asp Phe His Phe Glu Val Phe Asn Phe Val
             20                  25                  30

CCG TGC AGC ATC TGC AGC AAC AAC CCG ACC TGC TGG GCG ATC TGC AAA        144
Pro Cys Ser Ile Cys Ser Asn Asn Pro Thr Cys Trp Ala Ile Cys Lys
         35                  40                  45

CGT ATC CCG AAC AAA                                                    159
Arg Ile Pro Asn Lys
         50
```

(2) INFORMATION FOR SEQ ID NO: 28:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..153
        (D) OTHER INFORMATION:/product= "G6A"
            /note= "sequence 140-190"

(xi) SEQUENCE DESCRIPTION: SEQ ID NO: 28:

```
CAG ACC CAG CCG AGC AAA CCG ACC ACC AAA CAG CGT CAG AAC AAA CCG         48
```

```
Gln Thr Gln Pro Ser Lys Pro Thr Thr Lys Gln Arg Gln Asn Lys Pro
  1               5                  10                  15

CCG AAC AAA CCG AAC AAC GAT TTC CAT TTC GAA GTG TTC AAC TTC GTG        96
Pro Asn Lys Pro Asn Asn Asp Phe His Phe Glu Val Phe Asn Phe Val
             20                  25                  30

CCG TGC AGC ATC TGC AGC AAC AAC CCG ACC TGC TGG GCG ATC TGC AAA       144
Pro Cys Ser Ile Cys Ser Asn Asn Pro Thr Cys Trp Ala Ile Cys Lys
         35                  40                  45

CGT ATC CCG                                                           153
Arg Ile Pro
         50
```

(2) INFORMATION FOR SEQ ID NO: 29:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..99
        (D) OTHER INFORMATION:/product= "G7A"
            /note= "sequence 158-190"

(xi) SEQUENCE DESCRIPTION: SEQ ID NO: 29:

```
AAA CCG AAC AAC GAT TTC CAT TTC GAA GTG TTC AAC TTC GTG CCG TGC        48
Lys Pro Asn Asn Asp Phe His Phe Glu Val Phe Asn Phe Val Pro Cys
  1               5                  10                  15

AGC ATC TGC AGC AAC AAC CCG ACC TGC TGG GCG ATC TGC AAA CGT ATC        96
Ser Ile Cys Ser Asn Asn Pro Thr Cys Trp Ala Ile Cys Lys Arg Ile
             20                  25                  30

CCG                                                                    99
Pro
```

(2) INFORMATION FOR SEQ ID NO: 30:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..183
        (D) OTHER INFORMATION:/product= "G200AdeltaC"
            /note= "sequence 140-200"

(xi) SEQUENCE DESCRIPTION: SEQ ID NO: 30:

```
CAG ACC CAG CCG AGC AAA CCG ACC ACC AAA CAG CGT CAG AAC AAA CCG        48
Gln Thr Gln Pro Ser Lys Pro Thr Thr Lys Gln Arg Gln Asn Lys Pro
  1               5                  10                  15

CCG AAC AAA CCG AAC AAC GAT TTC CAT TTC GAA GTG TTC AAC TTC GTG        96
Pro Asn Lys Pro Asn Asn Asp Phe His Phe Glu Val Phe Asn Phe Val
             20                  25                  30

CCG AGC AGC ATC TGC AGC AAC AAC CCG ACC TGC TGG GCG ATC AGC AAA       144
Pro Ser Ser Ile Cys Ser Asn Asn Pro Thr Cys Trp Ala Ile Ser Lys
         35                  40                  45

CGT ATC CCG AAC AAA AAA CCG GGC AAA AAA ACC ACG ACC                   183
Arg Ile Pro Asn Lys Lys Pro Gly Lys Lys Thr Thr Thr
         50                  55                  60
```

(2) INFORMATION FOR SEQ ID NO: 31:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..177
        (D) OTHER INFORMATION:/product= "G198AdeltaC"
           /note= "sequence 140-198"

(xi) SEQUENCE DESCRIPTION: SEQ ID NO: 31:

```
CAG ACC CAG CCG AGC AAA CCG ACC ACC AAA CAG CGT CAG AAC AAA CCG        48
Gln Thr Gln Pro Ser Lys Pro Thr Thr Lys Gln Arg Gln Asn Lys Pro
  1               5                  10                  15

CCG AAC AAA CCG AAC AAC GAT TTC CAT TTC GAA GTG TTC AAC TTC GTG        96
Pro Asn Lys Pro Asn Asn Asp Phe His Phe Glu Val Phe Asn Phe Val
             20                  25                  30

CCG AGC AGC ATC TGC AGC AAC AAC CCG ACC TGC TGG GCG ATC AGC AAA       144
Pro Ser Ser Ile Cys Ser Asn Asn Pro Thr Cys Trp Ala Ile Ser Lys
         35                  40                  45

CGT ATC CCG AAC AAA AAA CCG GGC AAA AAA ACC                           177
Arg Ile Pro Asn Lys Lys Pro Gly Lys Lys Thr
     50                  55
```

(2) INFORMATION FOR SEQ ID NO: 32:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..171
        (D) OTHER INFORMATION:/product= "G196AdeltaC"
           /note= "sequence 140-196"

(xi) SEQUENCE DESCRIPTION: SEQ ID NO: 32:

```
CAG ACC CAG CCG AGC AAA CCG ACC ACC AAA CAG CGT CAG AAC AAA CCG        48
Gln Thr Gln Pro Ser Lys Pro Thr Thr Lys Gln Arg Gln Asn Lys Pro
  1               5                  10                  15

CCG AAC AAA CCG AAC AAC GAT TTC CAT TTC GAA GTG TTC AAC TTC GTG        96
Pro Asn Lys Pro Asn Asn Asp Phe His Phe Glu Val Phe Asn Phe Val
             20                  25                  30

CCG AGC AGC ATC TGC AGC AAC AAC CCG ACC TGC TGG GCG ATC AGC AAA       144
Pro Ser Ser Ile Cys Ser Asn Asn Pro Thr Cys Trp Ala Ile Ser Lys
         35                  40                  45

CGT ATC CCG AAC AAA AAA CCG GGC AAA                                   171
Arg Ile Pro Asn Lys Lys Pro Gly Lys
     50                  55
```

(2) INFORMATION FOR SEQ ID NO: 33:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: peptide (ix) FEATURE:
    (A) NAME/KEY: CDS
    (B) LOCATION:1..165
    (D) OTHER INFORMATION:/product= "G194AdeltaC"
        /note= "sequence 140-194"

(xi) SEQUENCE DESCRIPTION: SEQ ID NO: 33:

```
CAG ACC CAG CCG AGC AAA CCG ACC ACC AAA CAG CGT CAG AAC AAA CCG      48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG      96
Pro Asn Lys Pro Asn Asn Asp Phe His Phe Glu Val Phe Asn Phe Val
            20                  25                  30

CCG AGC AGC ATC TGC AGC AAC AAC CCG ACC TGC TGG GCG ATC AGC AAA     144
Pro Ser Ser Ile Cys Ser Asn Asn Pro Thr Cys Trp Ala Ile Ser Lys
        35                  40                  45

CGT ATC CCG AAC AAA AAA CCG                                         165
Arg Ile Pro Asn Lys Lys Pro
 50                  55
```

(2) INFORMATION FOR SEQ ID NO: 34:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..159
        (D) OTHER INFORMATION:/product= "G192AdeltaC"
            /note= "sequence 140-192"

(xi) SEQUENCE DESCRIPTION: SEQ ID NO: 34:

```
CAG ACC CAG CCG AGC AAA CCG ACC ACC AAA CAG CGT CAG AAC AAA CCG      48
Gln Thr Gln Pro Ser Lys Pro Thr Thr Lys Gln Arg Gln Asn Lys Pro
 1               5                  10                  15

CCG AAC AAA CCG AAC AAC GAT TTC CAT TTC GAA GTG TTC AAC TTC GTG      96
Pro Asn Lys Pro Asn Asn Asp Phe His Phe Glu Val Phe Asn Phe Val
            20                  25                  30

CCG AGC AGC ATC TGC AGC AAC AAC CCG ACC TGC TGG GCG ATC AGC AAA     144
Pro Ser Ser Ile Cys Ser Asn Asn Pro Thr Cys Trp Ala Ile Ser Lys
        35                  40                  45

CGT ATC CCG AAC AAA                                                 159
Arg Ile Pro Asn Lys
 50
```

(2) INFORMATION FOR SEQ ID NO: 35:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..153
        (D) OTHER INFORMATION:/product= "G6AdeltaC"
            /note= "sequence 140-190"

6,113,911

49

50

-continued (xi) SEQUENCE DESCRIPTION: SEQ ID NO: 35:

```
CAG ACC CAG CCG AGC AAA CCG ACC ACC AAA CAG CGT CAG AAC AAA CCG        48
Gln Thr Gln Pro Ser Lys Pro Thr Thr Lys Gln Arg Gln Asn Lys Pro
  1               5                  10                  15

CCG AAC AAA CCG AAC AAC GAT TTC CAT TTC GAA GTG TTC AAC TTC GTG        96
Pro Asn Lys Pro Asn Asn Asp Phe His Phe Glu Val Phe Asn Phe Val
                 20                  25                  30

CCG AGC AGC ATC TGC AGC AAC AAC CCG ACC TGC TGG GCG ATC AGC AAA       144
Pro Ser Ser Ile Cys Ser Asn Asn Pro Thr Cys Trp Ala Ile Ser Lys
             35                  40                  45

CGT ATC CCG                                                           153
Arg Ile Pro
         50
```

(2) INFORMATION FOR SEQ ID NO: 36:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: peptide
    (ix) FEATURE:
        (A) NAME/KEY: CDS
        (B) LOCATION:1..99
        (D) OTHER INFORMATION:/product= "G7AdeltaC"
           /note= "sequence 158-190"

(xi) SEQUENCE DESCRIPTION: SEQ ID NO: 36:

```
AAA CCG AAC AAC GAT TTC CAT TTC GAA GTG TTC AAC TTC GTG CCG AGC        48
Lys Pro Asn Asn Asp Phe His Phe Glu Val Phe Asn Phe Val Pro Ser
  1               5                  10                  15

AGC ATC TGC AGC AAC AAC CCG ACC TGC TGG GCG ATC AGC AAA CGT ATC        96
Ser Ile Cys Ser Asn Asn Pro Thr Cys Trp Ala Ile Ser Lys Arg Ile
                 20                  25                  30

CCG                                                                    99
Pro
```

(2) INFORMATION FOR SEQ ID NO: 37:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..183
        (D) OTHER INFORMATION:/product= "G200B"
           /note= "sequence 140-200"

(xi) SEQUENCE DESCRIPTION: SEQ ID NO: 37:

```
AGC ACC CAG ACC AAC AAA CCG AGC ACC AAA AGC CGT AGC AAA AAC CCG        48
Ser Thr Gln Thr Asn Lys Pro Ser Thr Lys Ser Arg Ser Lys Asn Pro
  1               5                  10                  15

CCG AAA AAA CCG AAA GAT GAT TAC CAC TTC GAA GTG TTC AAC TTC GTG        96
Pro Lys Lys Pro Lys Asp Asp Tyr His Phe Glu Val Phe Asn Phe Val
                 20                  25                  30

CCC TGC AGC ATC TGC GGC AAC AAC CAG CTG TGC AAA AGC ATC TGC AAA       144
Pro Cys Ser Ile Cys Gly Asn Asn Gln Leu Cys Lys Ser Ile Cys Lys
             35                  40                  45

ACC ATC CCG AGC AAC AAA CCG AAA AAG AAA CCG ACC ATC                   183
```

```
Thr Ile Pro Ser Asn Lys Pro Lys Lys Lys Pro Thr Ile
    50                  55                  60
```

(2) INFORMATION FOR SEQ ID NO: 38:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..177
        (D) OTHER INFORMATION:/product= "G198B"
            /note= "sequence 140-198"

(xi) SEQUENCE DESCRIPTION: SEQ ID NO: 38:

```
AGC ACC CAG ACC AAC AAA CCG AGC ACC AAA AGC CGT AGC AAA AAC CCG        48
Ser Thr Gln Thr Asn Lys Pro Ser Thr Lys Ser Arg Ser Lys Asn Pro
1               5                   10                  15

CCG AAA AAA CCG AAA GAT GAT TAC CAC TTC GAA GTG TTC AAC TTC GTG        96
Pro Lys Lys Pro Lys Asp Asp Tyr His Phe Glu Val Phe Asn Phe Val
            20                  25                  30

CCC TGC AGC ATC TGC GGC AAC AAC CAG CTG TGC AAA AGC ATC TGC AAA       144
Pro Cys Ser Ile Cys Gly Asn Asn Gln Leu Cys Lys Ser Ile Cys Lys
        35                  40                  45

ACC ATC CCG AGC AAC AAA CCG AAA AAG AAA CCG                           177
Thr Ile Pro Ser Asn Lys Pro Lys Lys Lys Pro
    50                  55
```

(2) INFORMATION FOR SEQ ID NO: 39:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..171
        (D) OTHER INFORMATION:/product= "G196B"
            /note= "sequence140-196"

(xi) SEQUENCE DESCRIPTION: SEQ ID NO: 39:

```
AGC ACC CAG ACC AAC AAA CCG AGC ACC AAA AGC CGT AGC AAA AAC CCG        48
Ser Thr Gln Thr Asn Lys Pro Ser Thr Lys Ser Arg Ser Lys Asn Pro
1               5                   10                  15

CCG AAA AAA CCG AAA GAT GAT TAC CAC TTC GAA GTG TTC AAC TTC GTG        96
Pro Lys Lys Pro Lys Asp Asp Tyr His Phe Glu Val Phe Asn Phe Val
            20                  25                  30

CCC TGC AGC ATC TGC GGC AAC AAC CAG CTG TGC AAA AGC ATC TGC AAA       144
Pro Cys Ser Ile Cys Gly Asn Asn Gln Leu Cys Lys Ser Ile Cys Lys
        35                  40                  45

ACC ATC CCG AGC AAC AAA CCG AAA AAG                                   171
Thr Ile Pro Ser Asn Lys Pro Lys Lys
    50                  55
```

(2) INFORMATION FOR SEQ ID NO: 40:

(i) SEQUENCE CHARACTERISTICS:
        (A) LENGTH: 165 base pairs
        (B) TYPE: nucleic acid (C) STRANDEDNESS: single
            (D) TOPOLOGY: linear (ii) MOLECULE TYPE: peptide (ix) FEATURE:
            (A) NAME/KEY: CDS
            (B) LOCATION:1..165
            (D) OTHER INFORMATION:/product= "G194B"
                /note= "sequence 140-194"

(xi) SEQUENCE DESCRIPTION: SEQ ID NO: 40:

```
AGC ACC CAG ACC AAC AAA CCG AGC ACC AAA AGC CGT AGC AAA AAC CCG        48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG        96
Pro Lys Lys Pro Lys Asp Asp Tyr His Phe Glu Val Phe Asn Phe Val
             20                  25                  30

CCC TGC AGC ATC TGC GGC AAC AAC CAG CTG TGC AAA AGC ATC TGC AAA       144
Pro Cys Ser Ile Cys Gly Asn Asn Gln Leu Cys Lys Ser Ile Cys Lys
         35                  40                  45

ACC ATC CCG AGC AAC AAA CCG                                           165
Thr Ile Pro Ser Asn Lys Pro
     50                  55
```

(2) INFORMATION FOR SEQ ID NO: 41:

(i) SEQUENCE CHARACTERISTICS:
            (A) LENGTH: 159 base pairs
            (B) TYPE: nucleic acid
            (C) STRANDEDNESS: single
            (D) TOPOLOGY: linear (ii) MOLECULE TYPE: peptide (ix) FEATURE:
            (A) NAME/KEY: CDS
            (B) LOCATION:1..159
            (D) OTHER INFORMATION:/product= "G192B"
                /note= "sequence 140-192"

(xi) SEQUENCE DESCRIPTION: SEQ ID NO: 41:

```
AGC ACC CAG ACC AAC AAA CCG AGC ACC AAA AGC CGT AGC AAA AAC CCG        48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG        96
Pro Lys Lys Pro Lys Asp Asp Tyr His Phe Glu Val Phe Asn Phe Val
             20                  25                  30

CCC TGC AGC ATC TGC GGC AAC AAC CAG CTG TGC AAA AGC ATC TGC AAA       144
Pro Cys Ser Ile Cys Gly Asn Asn Gln Leu Cys Lys Ser Ile Cys Lys
         35                  40                  45

ACC ATC CCG AGC AAC                                                   159
Thr Ile Pro Ser Asn
     50
```

(2) INFORMATION FOR SEQ ID NO: 42:

(i) SEQUENCE CHARACTERISTICS:
            (A) LENGTH: 153 base pairs
            (B) TYPE: nucleic acid
            (C) STRANDEDNESS: single
            (D) TOPOLOGY: linear (ii) MOLECULE TYPE: peptide (ix) FEATURE:
            (A) NAME/KEY: CDS
            (B) LOCATION:1..153
            (D) OTHER INFORMATION:/product= "G6B"

/note= "sequence 140-190"

(xi) SEQUENCE DESCRIPTION: SEQ ID NO: 42:

| | | |
|---|---|---|
| AGC ACC CAG ACC AAC AAA CCG AGC ACC AAA AGC CGT AGC AAA AAC CCG<br>Ser Thr Gln Thr Asn Lys Pro Ser Thr Lys Ser Arg Ser Lys Asn Pro<br>1               5                   10                  15 | 48 |
| CCG AAA AAA CCG AAA GAT GAT TAC CAC TTC GAA GTG TTC AAC TTC GTG<br>Pro Lys Lys Pro Lys Asp Asp Tyr His Phe Glu Val Phe Asn Phe Val<br>            20                  25                  30 | 96 |
| CCC TGC AGC ATC TGC GGC AAC AAC CAG CTG TGC AAA AGC ATC TGC AAA<br>Pro Cys Ser Ile Cys Gly Asn Asn Gln Leu Cys Lys Ser Ile Cys Lys<br>        35                  40                  45 | 144 |
| ACC ATC CCG<br>Thr Ile Pro<br>50 | 153 |

(2) INFORMATION FOR SEQ ID NO: 43:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..99
        (D) OTHER INFORMATION:/product= "G7B"
            /note= "sequence 158-190"

(xi) SEQUENCE DESCRIPTION: SEQ ID NO: 43:

| | |
|---|---|
| AAA CCG AAA GAT GAT TAC CAC TTC GAA GTG TTC AAC TTC GTG CCC TGC<br>Lys Pro Lys Asp Asp Tyr His Phe Glu Val Phe Asn Phe Val Pro Cys<br>1               5                   10                  15 | 48 |
| AGC ATC TGC GGC AAC AAC CAG CTG TGC AAA AGC ATC TGC AAA ACC ATC<br>Ser Ile Cys Gly Asn Asn Gln Leu Cys Lys Ser Ile Cys Lys Thr Ile<br>            20                  25                  30 | 96 |
| CCG<br>Pro | 99 |

(2) INFORMATION FOR SEQ ID NO: 44:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..183
        (D) OTHER INFORMATION:/product= "G200BdeltaC"
            /note= "sequence 140-200"

(xi) SEQUENCE DESCRIPTION: SEQ ID NO: 44:

| | |
|---|---|
| AGC ACC CAG ACC AAC AAA CCG AGC ACC AAA AGC CGT AGC AAA AAC CCG<br>Ser Thr Gln Thr Asn Lys Pro Ser Thr Lys Ser Arg Ser Lys Asn Pro<br>1               5                   10                  15 | 48 |
| CCG AAA AAA CCG AAA GAT GAT TAC CAC TTC GAA GTG TTC AAC TTC GTG<br>Pro Lys Lys Pro Lys Asp Asp Tyr His Phe Glu Val Phe Asn Phe Val<br>            20                  25                  30 | 96 |
| CCC AGC AGC ATC TGC GGC AAC AAC CAG CTG TGC AAA AGC ATC AGC AAA<br>Pro Ser Ser Ile Cys Gly Asn Asn Gln Leu Cys Lys Ser Ile Ser Lys | 144 |

```
                    35                  40                  45
ACC ATC CCG AGC AAC AAA CCG AAA AAG AAA CCG ACC ATC                      183
Thr Ile Pro Ser Asn Lys Pro Lys Lys Lys Pro Thr Ile
 50                  55                  60

(2) INFORMATION FOR SEQ ID NO: 45:

(i) SEQUENCE CHARACTERISTICS:
          (A) LENGTH: 177 base pairs
          (B) TYPE: nucleic acid
          (C) STRANDEDNESS: single
          (D) TOPOLOGY: linear (ii) MOLECULE TYPE: peptide (ix) FEATURE:
          (A) NAME/KEY: CDS
          (B) LOCATION:1..177
          (D) OTHER INFORMATION:/product= "G198BdeltaC"
               /note= "sequence 140-198"

(xi) SEQUENCE DESCRIPTION: SEQ ID NO: 45:

AGC ACC CAG ACC AAC AAA CCG AGC ACC AAA AGC CGT AGC AAA AAC CCG           48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG           96
Pro Lys Lys Pro Lys Asp Asp Tyr His Phe Glu Val Phe Asn Phe Val
                 20                  25                  30

CCC AGC AGC ATC TGC GGC AAC AAC CAG CTG TGC AAA AGC ATC AGC AAA          144
Pro Ser Ser Ile Cys Gly Asn Asn Gln Leu Cys Lys Ser Ile Ser Lys
             35                  40                  45

ACC ATC CCG AGC AAC AAA CCG AAA AAG AAA CCG                              177
Thr Ile Pro Ser Asn Lys Pro Lys Lys Lys Pro
 50                  55

(2) INFORMATION FOR SEQ ID NO: 46:

(i) SEQUENCE CHARACTERISTICS:
          (A) LENGTH: 171 base pairs
          (B) TYPE: nucleic acid
          (C) STRANDEDNESS: single
          (D) TOPOLOGY: linear (ii) MOLECULE TYPE: peptide (ix) FEATURE:
          (A) NAME/KEY: CDS
          (B) LOCATION:1..171
          (D) OTHER INFORMATION:/product= "G196BdeltaC"
               /note= "sequence 140-196"

(xi) SEQUENCE DESCRIPTION: SEQ ID NO: 46:

AGC ACC CAG ACC AAC AAA CCG AGC ACC AAA AGC CGT AGC AAA AAC CCG           48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG           96
Pro Lys Lys Pro Lys Asp Asp Tyr His Phe Glu Val Phe Asn Phe Val
                 20                  25                  30

CCC AGC AGC ATC TGC GGC AAC AAC CAG CTG TGC AAA AGC ATC AGC AAA          144
Pro Ser Ser Ile Cys Gly Asn Asn Gln Leu Cys Lys Ser Ile Ser Lys
             35                  40                  45

ACC ATC CCG AGC AAC AAA CCG AAA AAG                                      171
Thr Ile Pro Ser Asn Lys Pro Lys Lys
 50                  55

(2) INFORMATION FOR SEQ ID NO: 47:
```

(i) SEQUENCE CHARACTERISTICS:
    (A) LENGTH: 165 base pairs
    (B) TYPE: nucleic acid
    (C) STRANDEDNESS: single
    (D) TOPOLOGY: linear (ii) MOLECULE TYPE: peptide (ix) FEATURE:
    (A) NAME/KEY: CDS
    (B) LOCATION:1..165
    (D) OTHER INFORMATION:/product= "G194BdeltaC"
        /note= "sequence 140-194"

(xi) SEQUENCE DESCRIPTION: SEQ ID NO: 47:

| | | | | | | | | | | | | | | | | |
|---|---|---|---|---|---|---|---|---|---|---|---|---|---|---|---|---|
| AGC | ACC | CAG | ACC | AAC | AAA | CCG | AGC | ACC | AAA | AGC | CGT | AGC | AAA | AAC | CCG | 48 |
| Ser | Thr | Gln | Thr | Asn | Lys | Pro | Ser | Thr | Lys | Ser | Arg | Ser | Lys | Asn | Pro | |
| 1 | | | | 5 | | | | | 10 | | | | | 15 | | |
| CCG | AAA | AAA | CCG | AAA | GAT | GAT | TAC | CAC | TTC | GAA | GTG | TTC | AAC | TTC | GTG | 96 |
| Pro | Lys | Lys | Pro | Lys | Asp | Asp | Tyr | His | Phe | Glu | Val | Phe | Asn | Phe | Val | |
| | | | 20 | | | | | 25 | | | | | 30 | | | |
| CCC | AGC | AGC | ATC | TGC | GGC | AAC | AAC | CAG | CTG | TGC | AAA | AGC | ATC | AGC | AAA | 144 |
| Pro | Ser | Ser | Ile | Cys | Gly | Asn | Asn | Gln | Leu | Cys | Lys | Ser | Ile | Ser | Lys | |
| | | 35 | | | | | 40 | | | | | 45 | | | | |
| ACC | ATC | CCG | AGC | AAC | AAA | CCG | | | | | | | | | | 165 |
| Thr | Ile | Pro | Ser | Asn | Lys | Pro | | | | | | | | | | |
| | 50 | | | | 55 | | | | | | | | | | | |

(2) INFORMATION FOR SEQ ID NO: 48:

(i) SEQUENCE CHARACTERISTICS:
    (A) LENGTH: 159 base pairs
    (B) TYPE: nucleic acid
    (C) STRANDEDNESS: single
    (D) TOPOLOGY: linear (ii) MOLECULE TYPE: peptide (ix) FEATURE:
    (A) NAME/KEY: CDS
    (B) LOCATION:1..159
    (D) OTHER INFORMATION:/product= "G192BdeltaC"
        /note= "sequence 140-192"

(xi) SEQUENCE DESCRIPTION: SEQ ID NO: 48:

| | | | | | | | | | | | | | | | | |
|---|---|---|---|---|---|---|---|---|---|---|---|---|---|---|---|---|
| AGC | ACC | CAG | ACC | AAC | AAA | CCG | AGC | ACC | AAA | AGC | CGT | AGC | AAA | AAC | CCG | 48 |
| Ser | Thr | Gln | Thr | Asn | Lys | Pro | Ser | Thr | Lys | Ser | Arg | Ser | Lys | Asn | Pro | |
| 1 | | | | 5 | | | | | 10 | | | | | 15 | | |
| CCG | AAA | AAA | CCG | AAA | GAT | GAT | TAC | CAC | TTC | GAA | GTG | TTC | AAC | TTC | GTG | 96 |
| Pro | Lys | Lys | Pro | Lys | Asp | Asp | Tyr | His | Phe | Glu | Val | Phe | Asn | Phe | Val | |
| | | | 20 | | | | | 25 | | | | | 30 | | | |
| CCC | AGC | AGC | ATC | TGC | GGC | AAC | AAC | CAG | CTG | TGC | AAA | AGC | ATC | AGC | AAA | 144 |
| Pro | Ser | Ser | Ile | Cys | Gly | Asn | Asn | Gln | Leu | Cys | Lys | Ser | Ile | Ser | Lys | |
| | | 35 | | | | | 40 | | | | | 45 | | | | |
| ACC | ATC | CCG | AGC | AAC | | | | | | | | | | | | 159 |
| Thr | Ile | Pro | Ser | Asn | | | | | | | | | | | | |
| | 50 | | | | | | | | | | | | | | | |

(2) INFORMATION FOR SEQ ID NO: 49:

(i) SEQUENCE CHARACTERISTICS:
    (A) LENGTH: 153 base pairs
    (B) TYPE: nucleic acid
    (C) STRANDEDNESS: single
    (D) TOPOLOGY: linear (ii) MOLECULE TYPE: peptide (ix) FEATURE:

(A) NAME/KEY: CDS
         (B) LOCATION: 1..153
         (D) OTHER INFORMATION:/product= "G6BdeltaC"
             /note= "sequence 140-190"

(xi) SEQUENCE DESCRIPTION: SEQ ID NO: 49:

AGC ACC CAG ACC AAC AAA CCG AGC ACC AAA AGC CGT AGC AAA AAC CCG     48
Ser Thr Gln Thr Asn Lys Pro Ser Thr Lys Ser Arg Ser Lys Asn Pro
 1               5                  10                  15

CCG AAA AAA CCG AAA GAT GAT TAC CAC TTC GAA GTG TTC AAC TTC GTG     96
Pro Lys Lys Pro Lys Asp Asp Tyr His Phe Glu Val Phe Asn Phe Val
             20                  25                  30

CCC AGC AGC ATC TGC GGC AAC AAC CAG CTG TGC AAA AGC ATC AGC AAA    144
Pro Ser Ser Ile Cys Gly Asn Asn Gln Leu Cys Lys Ser Ile Ser Lys
         35                  40                  45

ACC ATC CCG                                                        153
Thr Ile Pro
    50

(2) INFORMATION FOR SEQ ID NO: 50:

(i) SEQUENCE CHARACTERISTICS:
         (A) LENGTH: 99 base pairs
         (B) TYPE: nucleic acid
         (C) STRANDEDNESS: single
         (D) TOPOLOGY: linear (ii) MOLECULE TYPE: peptide (ix) FEATURE:
         (A) NAME/KEY: CDS
         (B) LOCATION: 1..99
         (D) OTHER INFORMATION:/product= "G7BdeltaC"
             /note= "sequence 158-190"

(xi) SEQUENCE DESCRIPTION: SEQ ID NO: 50:

AAA CCG AAA GAT GAT TAC CAC TTC GAA GTG TTC AAC TTC GTG CCC AGC     48
Lys Pro Lys Asp Asp Tyr His Phe Glu Val Phe Asn Phe Val Pro Ser
 1               5                  10                  15

AGC ATC TGC GGC AAC AAC CAG CTG TGC AAA AGC ATC AGC AAA ACC ATC     96
Ser Ile Cys Gly Asn Asn Gln Leu Cys Lys Ser Ile Ser Lys Thr Ile
             20                  25                  30

CCG                                                                 99
Pro (2) INFORMATION FOR SEQ ID NO: 51:

(i) SEQUENCE CHARACTERISTICS:
         (A) LENGTH: 303 base pairs
         (B) TYPE: nucleic acid
         (C) STRANDEDNESS: single
         (D) TOPOLOGY: linear (ii) MOLECULE TYPE: peptide (ix) FEATURE:
         (A) NAME/KEY: CDS
         (B) LOCATION: 1..303
         (D) OTHER INFORMATION:/product= "G2V"
             /note= "sequence 130-230"

(xi) SEQUENCE DESCRIPTION: SEQ ID NO: 51:

CAA AAC AGA AAA ATC AAA GGT CAA TCA ACA CTA CCA GCC ACA AGA AAA     48
Gln Asn Arg Lys Ile Lys Gly Gln Ser Thr Leu Pro Ala Thr Arg Lys
 1               5                  10                  15

CCA CCA ATT AAT CCA TCA GGA AGC ATC CCA CCA GAA AAC CAT CAA GAC     96
Pro Pro Ile Asn Pro Ser Gly Ser Ile Pro Pro Glu Asn His Gln Asp
             20                  25                  30

```
CAC AAC AAC TTC CAA ACA CTC CCC TAT GTT CCC TGC AGT ACA TGT GAA        144
His Asn Asn Phe Gln Thr Leu Pro Tyr Val Pro Cys Ser Thr Cys Glu
         35                  40                  45

GGT AAT CTT GCA TGC TTA TCA CTC TGC CAT ATT GAG ACG GAA AGA GCA        192
Gly Asn Leu Ala Cys Leu Ser Leu Cys His Ile Glu Thr Glu Arg Ala
 50                  55                  60

CCA AGC AGA GCA CCA ACA ATC ACC CTC AAA AAG ACA CCA AAA CCA AAA        240
Pro Ser Arg Ala Pro Thr Ile Thr Leu Lys Lys Thr Pro Lys Pro Lys
 65                  70                  75                  80

ACC ACA AAA AAG CCA ACC AAG ACA ACA ATC CAT CAC AGA ACC AGC CCA        288
Thr Thr Lys Lys Pro Thr Lys Thr Thr Ile His His Arg Thr Ser Pro
             85                  90                  95

GAA ACC AAA CTG CAA                                                    303
Glu Thr Lys Leu Gln
            100
```

(2) INFORMATION FOR SEQ ID NO: 52:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..303
        (D) OTHER INFORMATION:/product= "G2VdeltaC"
           /note= "sequence 130-230"

(xi) SEQUENCE DESCRIPTION: SEQ ID NO: 52:

```
CAA AAC AGA AAA ATC AAA GGT CAA TCA ACA CTA CCA GCC ACA AGA AAA         48
Gln Asn Arg Lys Ile Lys Gly Gln Ser Thr Leu Pro Ala Thr Arg Lys
  1               5                  10                  15

CCA CCA ATT AAT CCA TCA GGA AGC ATC CCA CCA GAA AAC CAT CAA GAC         96
Pro Pro Ile Asn Pro Ser Gly Ser Ile Pro Pro Glu Asn His Gln Asp
             20                  25                  30

CAC AAC AAC TTC CAA ACA CTC CCC TAT GTT CCC AGC AGT ACA TGT GAA        144
His Asn Asn Phe Gln Thr Leu Pro Tyr Val Pro Ser Ser Thr Cys Glu
         35                  40                  45

GGT AAT CTT GCA TGC TTA TCA CTC AGC CAT ATT GAG ACG GAA AGA GCA        192
Gly Asn Leu Ala Cys Leu Ser Leu Ser His Ile Glu Thr Glu Arg Ala
 50                  55                  60

CCA AGC AGA GCA CCA ACA ATC ACC CTC AAA AAG ACA CCA AAA CCA AAA        240
Pro Ser Arg Ala Pro Thr Ile Thr Leu Lys Lys Thr Pro Lys Pro Lys
 65                  70                  75                  80

ACC ACA AAA AAG CCA ACC AAG ACA ACA ATC CAT CAC AGA ACC AGC CCA        288
Thr Thr Lys Lys Pro Thr Lys Thr Thr Ile His His Arg Thr Ser Pro
             85                  90                  95

GAA ACC AAA CTG CAA                                                    303
Glu Thr Lys Leu Gln
            100
```

(2) INFORMATION FOR SEQ ID NO: 53:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..183
        (D) OTHER INFORMATION:/product= "G200V"
            /note= "sequence 140-200"

(xi) SEQUENCE DESCRIPTION: SEQ ID NO: 53:

```
CTA CCA GCC ACA AGA AAA CCA CCA ATT AAT CCA TCA GGA AGC ATC CCA        48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT        96
Pro Glu Asn His Gln Asp His Asn Asn Phe Gln Thr Leu Pro Tyr Val
                20                  25                  30

CCC TGC AGT ACA TGT GAA GGT AAT CTT GCA TGC TTA TCA CTC TGC CAT       144
Pro Cys Ser Thr Cys Glu Gly Asn Leu Ala Cys Leu Ser Leu Cys His
            35                  40                  45

ATT GAG ACG GAA AGA GCA CCA AGC AGA GCA CCA ACA ATC                   183
Ile Glu Thr Glu Arg Ala Pro Ser Arg Ala Pro Thr Ile
    50                  55                  60
```

(2) INFORMATION FOR SEQ ID NO: 54:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..177
        (D) OTHER INFORMATION:/product= "G198V"
            /note= "sequence 140-198"

(xi) SEQUENCE DESCRIPTION: SEQ ID NO: 54:

```
CTA CCA GCC ACA AGA AAA CCA CCA ATT AAT CCA TCA GGA AGC ATC CCA        48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT        96
Pro Glu Asn His Gln Asp His Asn Asn Phe Gln Thr Leu Pro Tyr Val
                20                  25                  30

CCC TGC AGT ACA TGT GAA GGT AAT CTT GCA TGC TTA TCA CTC TGC CAT       144
Pro Cys Ser Thr Cys Glu Gly Asn Leu Ala Cys Leu Ser Leu Cys His
            35                  40                  45

ATT GAG ACG GAA AGA GCA CCA AGC AGA GCA CCA                           177
Ile Glu Thr Glu Arg Ala Pro Ser Arg Ala Pro
    50                  55
```

(2) INFORMATION FOR SEQ ID NO: 55:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..171
        (D) OTHER INFORMATION:/product= "G196V"
            /note= "sequence 140-196"

(xi) SEQUENCE DESCRIPTION: SEQ ID NO: 55:

```
CTA CCA GCC ACA AGA AAA CCA CCA ATT AAT CCA TCA GGA AGC ATC CCA        48
```

-continued

```
Leu Pro Ala Thr Arg Lys Pro Pro Ile Asn Pro Ser Gly Ser Ile Pro
  1               5                   10                  15

CCA GAA AAC CAT CAA GAC CAC AAC AAC TTC CAA ACA CTC CCC TAT GTT         96
Pro Glu Asn His Gln Asp His Asn Asn Phe Gln Thr Leu Pro Tyr Val
             20                  25                  30

CCC TGC AGT ACA TGT GAA GGT AAT CTT GCA TGC TTA TCA CTC TGC CAT        144
Pro Cys Ser Thr Cys Glu Gly Asn Leu Ala Cys Leu Ser Leu Cys His
             35                  40                  45

ATT GAG ACG GAA AGA GCA CCA AGC AGA                                    171
Ile Glu Thr Glu Arg Ala Pro Ser Arg
 50                  55
```

(2) INFORMATION FOR SEQ ID NO: 56:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..165
        (D) OTHER INFORMATION:/product= "G194V"
            /note= "sequence 140-194"

(xi) SEQUENCE DESCRIPTION: SEQ ID NO: 56:

```
CTA CCA GCC ACA AGA AAA CCA CCA ATT AAT CCA TCA GGA AGC ATC CCA         48
Leu Pro Ala Thr Arg Lys Pro Pro Ile Asn Pro Ser Gly Ser Ile Pro
  1               5                   10                  15

CCA GAA AAC CAT CAA GAC CAC AAC AAC TTC CAA ACA CTC CCC TAT GTT         96
Pro Glu Asn His Gln Asp His Asn Asn Phe Gln Thr Leu Pro Tyr Val
             20                  25                  30

CCC TGC AGT ACA TGT GAA GGT AAT CTT GCA TGC TTA TCA CTC TGC CAT        144
Pro Cys Ser Thr Cys Glu Gly Asn Leu Ala Cys Leu Ser Leu Cys His
             35                  40                  45

ATT GAG ACG GAA AGA GCA CCA                                            165
Ile Glu Thr Glu Arg Ala Pro
 50
```

(2) INFORMATION FOR SEQ ID NO: 57:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..159
        (D) OTHER INFORMATION:/product= "G192V"
            /note= "sequence 140-192"

(xi) SEQUENCE DESCRIPTION: SEQ ID NO: 57:

```
CTA CCA GCC ACA AGA AAA CCA CCA ATT AAT CCA TCA GGA AGC ATC CCA         48
Leu Pro Ala Thr Arg Lys Pro Pro Ile Asn Pro Ser Gly Ser Ile Pro
  1               5                   10                  15

CCA GAA AAC CAT CAA GAC CAC AAC AAC TTC CAA ACA CTC CCC TAT GTT         96
Pro Glu Asn His Gln Asp His Asn Asn Phe Gln Thr Leu Pro Tyr Val
             20                  25                  30

CCC TGC AGT ACA TGT GAA GGT AAT CTT GCA TGC TTA TCA CTC TGC CAT        144
Pro Cys Ser Thr Cys Glu Gly Asn Leu Ala Cys Leu Ser Leu Cys His
```

```
                35                  40                  45
ATT GAG ACG GAA AGA                                                          159
Ile Glu Thr Glu Arg
 50
```

(2) INFORMATION FOR SEQ ID NO: 58:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..153
        (D) OTHER INFORMATION:/product= "G6V"
            /note= "sequence 140-190"

(xi) SEQUENCE DESCRIPTION: SEQ ID NO: 58:

```
CTA CCA GCC ACA AGA AAA CCA CCA ATT AAT CCA TCA GGA AGC ATC CCA               48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT               96
Pro Glu Asn His Gln Asp His Asn Asn Phe Gln Thr Leu Pro Tyr Val
            20                  25                  30

CCC TGC AGT ACA TGT GAA GGT AAT CTT GCA TGC TTA TCA CTC TGC CAT              144
Pro Cys Ser Thr Cys Glu Gly Asn Leu Ala Cys Leu Ser Leu Cys His
        35                  40                  45

ATT GAG ACG                                                                  153
Ile Glu Thr
     50
```

(2) INFORMATION FOR SEQ ID NO: 59:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..99
        (D) OTHER INFORMATION:/product= "G7V"
            /note= "sequence 158-190"

(xi) SEQUENCE DESCRIPTION: SEQ ID NO: 59:

```
AAC CAT CAA GAC CAC AAC AAC TTC CAA ACA CTC CCC TAT GTT CCC TGC               48
Asn His Gln Asp His Asn Asn Phe Gln Thr Leu Pro Tyr Val Pro Cys
 1               5                  10                  15

AGT ACA TGT GAA GGT AAT CTT GCA TGC TTA TCA CTC TGC CAT ATT GAG               96
Ser Thr Cys Glu Gly Asn Leu Ala Cys Leu Ser Leu Cys His Ile Glu
            20                  25                  30

ACG                                                                           99
Thr
```

(2) INFORMATION FOR SEQ ID NO: 60:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: peptide (ix) FEATURE:
    (A) NAME/KEY: CDS
    (B) LOCATION:1..183
    (D) OTHER INFORMATION:/product= "G200VdeltaC"
        /note= "sequence 140-200"

(xi) SEQUENCE DESCRIPTION: SEQ ID NO: 60:

| CTA CCA GCC ACA AGA AAA CCA CCA ATT AAT CCA TCA GGA AGC ATC CCA | 48 |
| Leu Pro Ala Thr Arg Lys Pro Pro Ile Asn Pro Ser Gly Ser Ile Pro | |
| 1               5                   10                  15 | |

| CCA GAA AAC CAT CAA GAC CAC AAC AAC TTC CAA ACA CTC CCC TAT GTT | 96 |
| Pro Glu Asn His Gln Asp His Asn Asn Phe Gln Thr Leu Pro Tyr Val | |
|             20                  25                  30 | |

| CCC AGC AGT ACA TGT GAA GGT AAT CTT GCA TGC TTA TCA CTC AGC CAT | 144 |
| Pro Ser Ser Thr Cys Glu Gly Asn Leu Ala Cys Leu Ser Leu Ser His | |
|         35                  40                  45 | |

| ATT GAG ACG GAA AGA GCA CCA AGC AGA GCA CCA ACA ATC | 183 |
| Ile Glu Thr Glu Arg Ala Pro Ser Arg Ala Pro Thr Ile | |
|     50                  55                  60 | |

(2) INFORMATION FOR SEQ ID NO: 61:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..177
        (D) OTHER INFORMATION:/product= "G198VdeltaC"
            /note= "sequence 140-198"

(xi) SEQUENCE DESCRIPTION: SEQ ID NO: 61:

| CTA CCA GCC ACA AGA AAA CCA CCA ATT AAT CCA TCA GGA AGC ATC CCA | 48 |
| Leu Pro Ala Thr Arg Lys Pro Pro Ile Asn Pro Ser Gly Ser Ile Pro | |
| 1               5                   10                  15 | |

| CCA GAA AAC CAT CAA GAC CAC AAC AAC TTC CAA ACA CTC CCC TAT GTT | 96 |
| Pro Glu Asn His Gln Asp His Asn Asn Phe Gln Thr Leu Pro Tyr Val | |
|             20                  25                  30 | |

| CCC AGC AGT ACA TGT GAA GGT AAT CTT GCA TGC TTA TCA CTC AGC CAT | 144 |
| Pro Ser Ser Thr Cys Glu Gly Asn Leu Ala Cys Leu Ser Leu Ser His | |
|         35                  40                  45 | |

| ATT GAG ACG GAA AGA GCA CCA AGC AGA GCA CCA | 177 |
| Ile Glu Thr Glu Arg Ala Pro Ser Arg Ala Pro | |
|     50                  55 | |

(2) INFORMATION FOR SEQ ID NO: 62:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..171
        (D) OTHER INFORMATION:/product= "G196VdeltaC"
            /note= "sequence 140-196"

(xi) SEQUENCE DESCRIPTION: SEQ ID NO: 62:

```
CTA CCA GCC ACA AGA AAA CCA CCA ATT AAT CCA TCA GGA AGC ATC CCA        48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT        96
Pro Glu Asn His Gln Asp His Asn Asn Phe Gln Thr Leu Pro Tyr Val
                20                  25                  30

CCC AGC AGT ACA TGT GAA GGT AAT CTT GCA TGC TTA TCA CTC AGC CAT       144
Pro Ser Ser Thr Cys Glu Gly Asn Leu Ala Cys Leu Ser Leu Ser His
             35                  40                  45

ATT GAG ACG GAA AGA GCA CCA AGC AGA                                   171
Ile Glu Thr Glu Arg Ala Pro Ser Arg
         50                  55
```

(2) INFORMATION FOR SEQ ID NO: 63:

(i) SEQUENCE CHARACTERISTICS:
      (A) LENGTH: 165 base pairs
      (B) TYPE: nucleic acid
      (C) STRANDEDNESS: single
      (D) TOPOLOGY: linear (ii) MOLECULE TYPE: peptide (ix) FEATURE:
      (A) NAME/KEY: CDS
      (B) LOCATION:1..165
      (D) OTHER INFORMATION:/product= "G194VdeltaC"
          /note= "sequence 140-194"

(xi) SEQUENCE DESCRIPTION: SEQ ID NO: 63:

```
CTA CCA GCC ACA AGA AAA CCA CCA ATT AAT CCA TCA GGA AGC ATC CCA        48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT        96
Pro Glu Asn His Gln Asp His Asn Asn Phe Gln Thr Leu Pro Tyr Val
                20                  25                  30

CCC AGC AGT ACA TGT GAA GGT AAT CTT GCA TGC TTA TCA CTC AGC CAT       144
Pro Ser Ser Thr Cys Glu Gly Asn Leu Ala Cys Leu Ser Leu Ser His
             35                  40                  45

ATT GAG ACG GAA AGA GCA CCA                                           165
Ile Glu Thr Glu Arg Ala Pro
         50                  55
```

(2) INFORMATION FOR SEQ ID NO: 64:

(i) SEQUENCE CHARACTERISTICS:
      (A) LENGTH: 159 base pairs
      (B) TYPE: nucleic acid
      (C) STRANDEDNESS: single
      (D) TOPOLOGY: linear (ii) MOLECULE TYPE: peptide (ix) FEATURE:
      (A) NAME/KEY: CDS
      (B) LOCATION:1..159
      (D) OTHER INFORMATION:/product= "G192VdeltaC"
          /note= "sequence 140-192"

(xi) SEQUENCE DESCRIPTION: SEQ ID NO: 64:

```
CTA CCA GCC ACA AGA AAA CCA CCA ATT AAT CCA TCA GGA AGC ATC CCA        48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT        96
Pro Glu Asn His Gln Asp His Asn Asn Phe Gln Thr Leu Pro Tyr Val
                20                  25                  30
```

```
CCC AGC AGT ACA TGT GAA GGT AAT CTT GCA TGC TTA TCA CTC AGC CAT      144
Pro Ser Ser Thr Cys Glu Gly Asn Leu Ala Cys Leu Ser Leu Ser His
        35                  40                  45

ATT GAG ACG GAA AGA                                                  159
Ile Glu Thr Glu Arg
 50
```

(2) INFORMATION FOR SEQ ID NO: 65:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..153
        (D) OTHER INFORMATION:/product= "G6VdeltaC"
            /note= "sequence 140-190"

(xi) SEQUENCE DESCRIPTION: SEQ ID NO: 65:

```
CTA CCA GCC ACA AGA AAA CCA CCA ATT AAT CCA TCA GGA AGC ATC CCA       48
Leu Pro Ala Thr Arg Lys Pro Pro Ile Asn Pro Ser Gly Ser Ile Pro
 1               5                  10                  15

CCA GAA AAC CAT CAA GAC CAC AAC AAC TTC CAA ACA CTC CCC TAT GTT       96
Pro Glu Asn His Gln Asp His Asn Asn Phe Gln Thr Leu Pro Tyr Val
            20                  25                  30

CCC AGC AGT ACA TGT GAA GGT AAT CTT GCA TGC TTA TCA CTC AGC CAT      144
Pro Ser Ser Thr Cys Glu Gly Asn Leu Ala Cys Leu Ser Leu Ser His
        35                  40                  45

ATT GAG ACG                                                          153
Ile Glu Thr
 50
```

(2) INFORMATION FOR SEQ ID NO: 66:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..99
        (D) OTHER INFORMATION:/product= "G7VdeltaC"
            /note= "sequence 158-190"

(xi) SEQUENCE DESCRIPTION: SEQ ID NO: 66:

```
AAC CAT CAA GAC CAC AAC AAC TTC CAA ACA CTC CCC TAT GTT CCC AGC       48
Asn His Gln Asp His Asn Asn Phe Gln Thr Leu Pro Tyr Val Pro Ser
 1               5                  10                  15

AGT ACA TGT GAA GGT AAT CTT GCA TGC TTA TCA CTC AGC CAT ATT GAG       96
Ser Thr Cys Glu Gly Asn Leu Ala Cys Leu Ser Leu Ser His Ile Glu
            20                  25                  30

ACG                                                                   99
Thr
```

(2) INFORMATION FOR SEQ ID NO: 67:

(i) SEQUENCE CHARACTERISTICS:
        (A) LENGTH: 51 base pairs

-continued

```
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..51
        (D) OTHER INFORMATION:/product= "G4V"
            /note= "sequence 171-187"

(xi) SEQUENCE DESCRIPTION: SEQ ID NO: 67:

GTT CCC TGC AGT ACA TGT GAA GGT AAT CTT GCA TGC TTA TCA CTC TGC      48
Val Pro Cys Ser Thr Cys Glu Gly Asn Leu Ala Cys Leu Ser Leu Cys
 1               5                  10                  15

CAT                                                                  51
His (2) INFORMATION FOR SEQ ID NO: 68:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..51
        (D) OTHER INFORMATION:/product= "G4VdeltaC"
            /note= "sequence 171-187"

(xi) SEQUENCE DESCRIPTION: SEQ ID NO: 68:

GTT CCC AGC AGT ACA TGT GAA GGT AAT CTT GCA TGC TTA TCA CTC AGC      48
Val Pro Ser Ser Thr Cys Glu Gly Asn Leu Ala Cys Leu Ser Leu Ser
 1               5                  10                  15

CAT                                                                  51
His (2) INFORMATION FOR SEQ ID NO: 69:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:12
        (D) OTHER INFORMATION:/product= "Orn"

(ix) FEATURE:
        (A) NAME/KEY: Peptide
        (B) LOCATION:16
        (D) OTHER INFORMATION:/product= "Orn"
            /note= "name : G4'V / sequence 171-187"

(xi) SEQUENCE DESCRIPTION: SEQ ID NO: 69:

Val Pro Asp Ser Thr Asp Glu Gly Asn Leu Ala Xaa Leu Ser Leu Xaa
 1               5                  10                  15

His (2) INFORMATION FOR SEQ ID NO: 70:
```

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:12
            (D) OTHER INFORMATION:/product= "Orn"
                /note= "name : G4'VdeltaC / sequence : 171-187"

(xi) SEQUENCE DESCRIPTION: SEQ ID NO: 70:

Val Pro Ser Ser Thr Asp Glu Gly Asn Leu Ala Xaa Leu Ser Leu Ser
1               5                   10                  15

His (2) INFORMATION FOR SEQ ID NO: 71:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: peptide (ix) FEATURE:
            (A) NAME/KEY: CDS
            (B) LOCATION:1..42
            (D) OTHER INFORMATION:/product= "G1V"
                /note= "sequence 174-187"

(xi) SEQUENCE DESCRIPTION: SEQ ID NO: 71:

AGT ACA TGT GAA GGT AAT CTT GCA TGC TTA TCA CTC TGC CAT          42
Ser Thr Cys Glu Gly Asn Leu Ala Cys Leu Ser Leu Cys His
1               5                   10

(2) INFORMATION FOR SEQ ID NO: 72:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: peptide (ix) FEATURE:
            (A) NAME/KEY: CDS
            (B) LOCATION:1..42
            (D) OTHER INFORMATION:/product= "G1VdeltaC"
                /note= "sequence 174-187"

(xi) SEQUENCE DESCRIPTION: SEQ ID NO: 72:

AGT ACA TGT GAA GGT AAT CTT GCA TGC TTA TCA CTC AGC CAT          42
Ser Thr Cys Glu Gly Asn Leu Ala Cys Leu Ser Leu Ser His
1               5                   10

(2) INFORMATION FOR SEQ ID NO: 73:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (ix) FEATURE:

(A) NAME/KEY: Peptide
        (B) LOCATION:9
        (D) OTHER INFORMATION:/product= "Orn"
            /note= "name : G1'VdeltaC / sequence 174-187"

(xi) SEQUENCE DESCRIPTION: SEQ ID NO: 73:

Ser Thr Asp Glu Gly Asn Leu Ala Xaa Leu Ser Leu Ser His
1               5                   10

(2) INFORMATION FOR SEQ ID NO: 74:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..657
        (D) OTHER INFORMATION:/product= "BB"

(xi) SEQUENCE DESCRIPTION: SEQ ID NO: 74:

| | |
|---|---|
| AAA TAT GGA GTA AGT GAC TAT TAC AAG AAT CTA ATC AAC AAT GCC AAA<br>Lys Tyr Gly Val Ser Asp Tyr Tyr Lys Asn Leu Ile Asn Asn Ala Lys<br>1               5                   10                  15 | 48 |
| ACT GTT GAA GGC GTA AAA GAC CTT CAA GCA CAA GTT GTT GAA TCA GCG<br>Thr Val Glu Gly Val Lys Asp Leu Gln Ala Gln Val Val Glu Ser Ala<br>                20                  25                  30 | 96 |
| AAG AAA GCG CGT ATT TCA GAA GCA ACA GAT GGC TTA TCT GAT TTC TTG<br>Lys Lys Ala Arg Ile Ser Glu Ala Thr Asp Gly Leu Ser Asp Phe Leu<br>            35                  40                  45 | 144 |
| AAA TCA CAA ACA CCT GCT GAA GAT ACT GTT AAA TCA ATT GAA TTA GCT<br>Lys Ser Gln Thr Pro Ala Glu Asp Thr Val Lys Ser Ile Glu Leu Ala<br>    50                  55                  60 | 192 |
| GAA GCT AAA GTC TTA GCT AAC AGA GAA CTT GAC AAA TAT GGA GTA AGT<br>Glu Ala Lys Val Leu Ala Asn Arg Glu Leu Asp Lys Tyr Gly Val Ser<br>65                  70                  75                  80 | 240 |
| GAC TAT CAC AAG AAC CTA ATC AAC AAT GCC AAA ACT GTT GAA GGT GTA<br>Asp Tyr His Lys Asn Leu Ile Asn Asn Ala Lys Thr Val Glu Gly Val<br>                85                  90                  95 | 288 |
| AAA GAC CTT CAA GCA CAA GTT GTT GAA TCA GCG AAG AAA GCG CGT ATT<br>Lys Asp Leu Gln Ala Gln Val Val Glu Ser Ala Lys Lys Ala Arg Ile<br>            100                 105                 110 | 336 |
| TCA GAA GCA ACA GAT GGC TTA TCT GAT TTC TTG AAA TCA CAA ACA CCT<br>Ser Glu Ala Thr Asp Gly Leu Ser Asp Phe Leu Lys Ser Gln Thr Pro<br>        115                 120                 125 | 384 |
| GCT GAA GAT ACT GTT AAA TCA ATT GAA TTA GCT GAA GCT AAA GTC TTA<br>Ala Glu Asp Thr Val Lys Ser Ile Glu Leu Ala Glu Ala Lys Val Leu<br>    130                 135                 140 | 432 |
| GCT AAC AGA GAA CTT GAC AAA TAT GGA GTA AGT GAC TAT TAC AAG AAC<br>Ala Asn Arg Glu Leu Asp Lys Tyr Gly Val Ser Asp Tyr Tyr Lys Asn<br>145                 150                 155                 160 | 480 |
| CTA ATC AAC AAT GCC AAA ACT GTT GAA GGT GTA AAA GCA CTG ATA GAT<br>Leu Ile Asn Asn Ala Lys Thr Val Glu Gly Val Lys Ala Leu Ile Asp<br>                165                 170                 175 | 528 |
| GAA ATT TTA GCT GCA TTA CCT AAG ACT GAC ACT TAC AAA TTA ATC CTT<br>Glu Ile Leu Ala Ala Leu Pro Lys Thr Asp Thr Tyr Lys Leu Ile Leu<br>            180                 185                 190 | 576 |
| AAT GGT AAA ACA TTG AAA GGC GAA ACA ACT ACT GAA GCT GTT GAT GCT<br>Asn Gly Lys Thr Leu Lys Gly Glu Thr Thr Thr Glu Ala Val Asp Ala<br>        195                 200                 205 | 624 |

```
GCT ACT GCA AGA TCT TTC AAT TTC CCT ATC CTC                              657
Ala Thr Ala Arg Ser Phe Asn Phe Pro Ile Leu
    210                 215

(2) INFORMATION FOR SEQ ID NO: 75:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION:1..324
        (D) OTHER INFORMATION:/product= "fragment BB"

(xi) SEQUENCE DESCRIPTION: SEQ ID NO: 75:

AAA TAT GGA GTA AGT GAC TAT CAC AAG AAC CTA ATC AAC AAT GCC AAA           48
Lys Tyr Gly Val Ser Asp Tyr His Lys Asn Leu Ile Asn Asn Ala Lys
1               5                   10                  15

ACT GTT GAA GGT GTA AAA GAC CTT CAA GCA CAA GTT GTT GAA TCA GCG           96
Thr Val Glu Gly Val Lys Asp Leu Gln Ala Gln Val Val Glu Ser Ala
            20                  25                  30

AAG AAA GCG CGT ATT TCA GAA GCA ACA GAT GGC TTA TCT GAT TTC TTG          144
Lys Lys Ala Arg Ile Ser Glu Ala Thr Asp Gly Leu Ser Asp Phe Leu
        35                  40                  45

AAA TCA CAA ACA CCT GCT GAA GAT ACT GTT AAA TCA ATT GAA TTA GCT          192
Lys Ser Gln Thr Pro Ala Glu Asp Thr Val Lys Ser Ile Glu Leu Ala
    50                  55                  60

GAA GCT AAA GTC TTA GCT AAC AGA GAA CTT GAC AAA TAT GGA GTA AGT          240
Glu Ala Lys Val Leu Ala Asn Arg Glu Leu Asp Lys Tyr Gly Val Ser
65                  70                  75                  80

GAC TAT TAC AAG AAC CTA ATC AAC AAT GCC AAA ACT GTT GAA GGT GTA          288
Asp Tyr Tyr Lys Asn Leu Ile Asn Asn Ala Lys Thr Val Glu Gly Val
            85                  90                  95

AAA GCA CTG ATA GAT GAA ATT TTA GCT GCA TTA CCT                          324
Lys Ala Leu Ile Asp Glu Ile Leu Ala Ala Leu Pro
        100                 105
```

PEPTIDE FRAGMENT OF RESPIRATORY SYNCYTIAL VIRUS PROTEIN G, IMMUNOGENIC AGENT, PHARMACEUTICAL COMPOSITION CONTAINING IT AND PREPARATION METHOD

The present invention relates to polypeptides which can be used especially in the preparation of immunogens and the obtainment of vaccine against respiratory syncytial virus (RSV) and to nucleotide sequences enabling them to be obtained. The invention likewise relates to an immune adjuvant protein extracted from Klebsiella pneumoniae, to compositions comprising the immunogenic polypeptides, possibly associated with such an adjuvant protein, and to their preparation process.

Respiratory syncytial virus (RSV) is the most frequent cause of respiratory illnesses in the newborn: bronchopneumopathies (bronchiolites). The WHO estimates each year 50 million cases of RSV attacks, from which 160,000 die in the entire world. There are two subgroups of the virus (subgroups A and B).

RSV is classified in the Paramyxoviridae family, a type of pneumovirus comprising a nonsegmented RNA genome, of negative polarity, coding for 10 specific proteins.

There is at present no vaccine available against RSV. Inactivated virus vaccines have been shown to be inefficaceous and have sometimes even aggravated the infections of nursing infants. In the 60's, vaccination attempts with formalin-inactivated RSV resulted in failure: instead of conferring protection at the time of reinfection due to RSV, the vaccine had the effect of aggravating the illness in the child.

The Application WO 87/04185 proposed to use structural proteins of RSV with a view to a vaccine, such as the envelope proteins called protein F (fusion protein) or protein G, a 22 Kd glycoprotein, a 9.5 Kd protein, or the major capsid protein (protein N).

The Application WO 89/02935 describes the protective properties of the entire protein F of RSV, possibly modified in monomeric or deacetylated form.

A series of fragments of protein F have been cloned with a view to investigating their neutralizing properties.

However, the immune vaccines tested to date have been shown to be inefficaceous or have induced a pulmonary pathology (bronchiolitis or peribronchitis).

At the present time, there is no in-depth treatment of infections due to RSV.

Infections due to RSV of the upper airways: treatment relies essentially on symptomatic medications identical to those for other viral infections.

Infections due to RSV of the lower airways: treatment in nursing infants relies on the maintenance of correct hydration, the aspiration of the secretions and the administration of oxygen if necessary. A positive effect has been observed with ribavirin, a nucleotide which is active in vitro against RSV.

It is for these reasons that an object of the present invention is a polypeptide which is useful especially in immunogen production, characterized in that it is carried by the peptide sequence between the amino acid residues 130 and 230 of the sequence of respiratory syncytial virus protein G, or by a sequence having at least 80% homology with said peptide sequence. This sequence differs slightly for the subgroups A and B of human RSV, or for bovine RSV. The invention comprises the sequences originating from human RSV subgroup A and B, or bovine RSV.

Protein G is an RSV envelope glycoprotein, of molecular weight of between 84 and 90 Kd, which is low in methionine.

The Applicant has demonstrated that the sequence between amino acids 130 and 230 of natural protein G is particularly appropriate for inducing an efficaceous protection against infection by RSV. The invention comprises the sequences originating from human RSV subgroup A or B, or bovine RSV.

More particularly, the present invention relates to polypeptides, which are useful especially as immunogenic element included in the above and which comprise the peptide sequence between the amino acid residues numbered 174 and 187 of RSV protein G (human, subgroups A and B, or bovine) or a sequence having at least 80% homology with the corresponding sequence.

Other peptide sequences adapted to the preparation of an immunogen included in said sequence of RSV protein G are formed by the sequence between the amino acid residues numbered 171 and 187 of human or bovine RSV protein G, or a sequence having at least 80% homology with the corresponding sequence. Other peptides of interest according to the present invention are carried by the sequence between the nucleotides numbered 158 and 190 of RSV protein G or a sequence having at least 80% homology with the corresponding sequence.

According to another method of carrying it out, the invention relates to peptides useful for the preparation of an immunogen and which have a sequence corresponding to the sequence between the amino acid residues numbered 140 and 200 of human or bovine RSV protein G, or a sequence having at least 80% homology with the corresponding sequence. Sequences starting with amino acid 140 of said RSV protein G and whose C-terminal end corresponds respectively to the amino acid 198, 196, 194, 192 or 190, as well as sequences having at least 80% homology with the sequence carried by these fragments, are particularly advantageous.

Among the variants of the above sequences, polypeptides may be mentioned which comprise a sequence in which:

a) the Cys amino acid in positions 173 and/or 186 has been replaced by an amino acid not forming a disulfide bridge, in particular serine, and/or b) the amino acids in positions 176 and 182 are capable of forming a covalent bridge other than a disulfide bridge, especially aspartic acid and ornithine.

Thus the polypeptide sequence 130–230 of RSV subgroup A can be used complete, in its native form. This sequence corresponds to the written sequence Seq id No.

In the same way, it is possible to use the complete polypeptide sequence 130–230 of RSV subgroup B in its native form. This sequence corresponds to the written sequence Seq id No. 2 (G2B).

The sequence id No. 1 will be written G2A in the remainder of the application.

The sequence id No. 2 will be written G2B in the remainder of the application.

Sequences having at least 80% homology with G2A or G2B are also appropriate.

The sequence between the amino acids 130 and 230 can be modified by the replacement of the cysteine residue in positions 173 and 186 by serine residues to obtain a peptide retaining good immunogenic properties, owing to maintenance of the loop formed by the Cys residues in positions 176 and 182. The amino acid and nucleotide sequences of this polypeptide for subgroup A are represented in seq id No. 3 (G2AδCys).

For subgroup B, the amino acid and nucleotide sequences are represented in seq id No. 4 (G2BδCys).

The peptide sequences will be written G2AδCys and G2BδCys.

According to another aspect, an object of the invention is a polypeptide which is useful for the preparation of immunogen, characterized in that it consists in the peptide sequence between the amino acid residues numbered 174 and 187 of RSV protein G or a sequence having at least 80% homology with said peptide sequence.

In this last sequence the peptide 174–187 subgroup A can have the sequence:
Seq id No. 5:
Ser Ile Cys Ser Asn Asn Pro Thr Cys Trp Ala Ile Cys Lys.
The peptide 174–187 subgroup B can have the sequence:
Seq id No. 6:
Ser-Ile-Cys-Gly-Asn-Asn-Gln-Leu-Cys-Lys-Ser-Ile-Cys-Lys.

The Cys residue in position 186 can also be replaced by a serine residue, so as to obtain the following sequence:
Seq id No. 7 for subgroup A:
Ser Ile Cys Ser Asn Asn Pro Thr Cys Trp Ala Ile Ser Lys.
Seq id No. 8 for subgroup B:
Ser-Ile-Cys-Gly-Asn-Asn-Gln-Leu-Cys-Lys-Ser-Ile-Ser-Lys.

In the sequence between residues 174 and 187 of the immunogenic peptide, according to one of the variants of the invention, the amino acid residues in positions 176 and 182 are respectively replaced by an aspartic acid and an ornithine, so as to obtain one of the following sequences:
Seq id No. 9 for subgroup A:
Ser Ile Asp Ser Asn Asn Pro Thr Orn Trp Ala Ile Cys Lys
Seq id No. 10 for subgroup B
Ser-Ile-Asp-Gly-Asn-Asn-Gln-Leu-Orn-Lys-Ser-Ile-Cys-Lys.
Seq id No. 11 for subgroup A:
Ser Ile Asp Ser Asn Asn Pro Thr Orn Trp Ala Ile Ser Lys.
Seq id No. 12 for subgroup B:
Ser-Ile-Asp-Gly-Asn-Asn-Gln-Leu-Orn-Lys-Ser-Ile-Ser-Lys.

The maintenance of the immunogenic properties is obtained owing to the replacement of the disulfide bridge (between the natural Cys residues) by an amide bridge between the positions 176 and 182.

Other sequences according to the invention such as defined above appear in the annex of the present application under the names SEQ ID No. 14 to SEQ ID No. 73.

An object of the invention is likewise a polypeptide which can be used as an immunogenic agent having one of the preceding sequences and which additionally comprises at least one cysteine residue in the N-terminal or C-terminal position.

The invention likewise comprises a polypeptide which consists of the peptide sequence between the amino acid residues numbered 130 and 230 of the RSV protein G sequence subgroup A and subgroup B, or of a sequence having 88% homology with said peptide sequence and which is in the form of a fusion protein with the receptor of human serum albumin, called BBG2AδC or BBG2BδC, or another linking protein. The sequence of the complete BB protein appears in the annex (Seq ID No. 74).

The invention likewise comprises the variants, for example glycosylated or sulfated, of the different peptides, whether these functions are natural or not.

The polypeptides can be prepared by peptide synthesis or by recombinant DNA techniques, which are known to the person skilled in the art.

In particular, the gene sequences coding for the epitope of approximately 100 amino acids can be prepared by solid-phase assembly of genes, and the corresponding protein expressed, for example, in *E. coli* by the intracellular route.

The nucleotide sequences (RNA or DNA) coding for the proteins or the polypeptides defined above are part of the invention.

Another object of the invention is an immunogenic agent which comprises a polypeptide such as defined above coupled to a carrier protein, in particular to an immune adjuvant protein.

Preferably, the polypeptide according to the invention is coupled to a carrier protein of the type OmpA of the external membrane of a bacterium of the genus Klebsiella, preferably in the form of a soluble conjugate.

The Applicant has been able to show that although the variants of the sequence 174–187 of the RSV protein G are weakly immunogenic, their coupling with such a protein induces a specific immune response.

The intensity of the immune response has been compared to that obtained with conventional adjuvants, such as coupling to the carrier KLH (keyhole limpet hemocyanin) coadministered with Freund's adjuvant, or coupling to the carrier protein TT (tetanus toxoid).

Particularly advantageous results are obtained for compositions comprising an immunogenic polypeptide according to the invention coupled to protein p40 of Klebsiella pneumoniae or a protein having 80% homology with protein p40.

More particularly, said polypeptide is coupled to a protein comprising the peptide sequence written Seq id No. 13.

The nucleotide sequence (DNA or RNA) coding for the protein comprising the sequence id No. 13 is comprised in the invention.

The immunogenic polypeptide can be coupled to the immune adjuvant protein by methods known to the person skilled in the art, such as:
Glutaraldehyde
Carbodiimide (e.g.: EDC: 1-(3dimethylaminopropyl)-3-ethylcarbodiimide).
Bis imido esters (e.g.: dimethyl adipimidate).
N-hydroxysuccinimidyl esters (e.g.: disuccinimidyl suberate).
For peptides comprising a supplementary cysteine in the N terminal or C terminal position:
Maleimido-N-hydroxysuccinimide esters (e.g.: MBS: maleimido benzoyl-N-hydroxysuccinimide ester).
N-succinimidyl bromoacetate.

The polypeptide can be conjugated to the carrier protein by a linking protein, for example the human serum albumin receptor (BB).

According to another aspect, an object of the invention is likewise a process for the preparation of a conjugated peptide inserted in a composition useful for prevention or treatment of infections with RSV, characterized in that:
a) the membrane lipopolysaccharides of bacteria of the genus Klebsiella are precipitated in the presence of a salt of a divalent cation and of detergents to recover the total membrane proteins in the supernatant,
b) the proteins are submitted to anion-exchange chromatography to separate the fraction containing the immune adjuvant protein,
c) the fraction containing the immune adjuvant protein is concentrated,
d) the immune adjuvant protein is conjugated with an immunogenic polypeptide such as defined above to form a soluble conjugate.

The divalent cation salt used in step a) is preferably a salt of calcium or of magnesium. After centrifugation, the proteins of the supernatant can be recovered in good yield by two precipitations with ethanol.

The membrane proteins, after resuspension, are separated on an anion-exchange column which can be used under industrial conditions. This chromatographic support is very stable and compatible with drastic pyrogen removal treatments, which was not the case with the chromatographic supports already described. On the other hand, elution of the protein can be carried out under isocratic conditions and not by application of an NaCl gradient (as described previously), which is particularly advantageous under industrial conditions.

According to a preferred method of carrying out the invention, step c) is followed by a second chromatography step, on a cation exchanger, and the fractions containing the adjuvant protein are recovered and concentrated. This supplementary step allows a better elimination of the lipopolysaccharides. The adjuvant protein is then conjugated to an immunogenic polypeptide according to the invention.

According to another aspect, the invention relates to a composition useful for the prevention and/or treatment of infections provoked by RSV, characterized in that it contains a polypeptide characterized above.

More particularly, the compositions additionally contain pharmaceutically acceptable excipients adapted for administration by the injectable route.

In fact, the Applicant has demonstrated that the injection of such compositions affords protection, not by a neutralizing effect, but by a systemic immune response of the body.

The humoral and cellular responses (IgM, IgG, IgA and T cells) are provoked by the product which likewise induces a long-term protection and an immunological memory against the RSV subgroups a and b.

With a view to the administration of the vaccine compositions by the subcutaneous route, it is desirable to have available soluble conjugate, which is difficult by the conventional methods.

It is for this reason that the invention likewise relates to a process for the preparation of a conjugate between an immunogenic peptide and a membrane protein of Klebsiella, in particular the protein p40 of K. pneumoniae, in which the coupling is carried out in the presence of glutaraldehyde at concentrations lower than or equal to 0.05%.

This coupling process considerably reduces the concentrations of glutaraldehyde in comparison with those usually used (2 times 0.01% instead of 1% approximately); the glutaraldehyde is added in 2 portions over a period of five days although the protocols described mention times of 24 hours.

These modifications have allowed the obtainment of a soluble conjugate, in a form adapted for subcutaneous administration.

The usual protocols (higher concentrations of glutaraldehyde and short times) are manifested by the formation of a thick gel (due to P40-P40 conjugation reactions, very probably), a form unfit for administration and manipulation in general.

The conjugated peptide can be frozen and used as such or lyophilized.

The examples which follow are intended to illustrate the invention without in any way limiting the range thereof.

Figure 2:
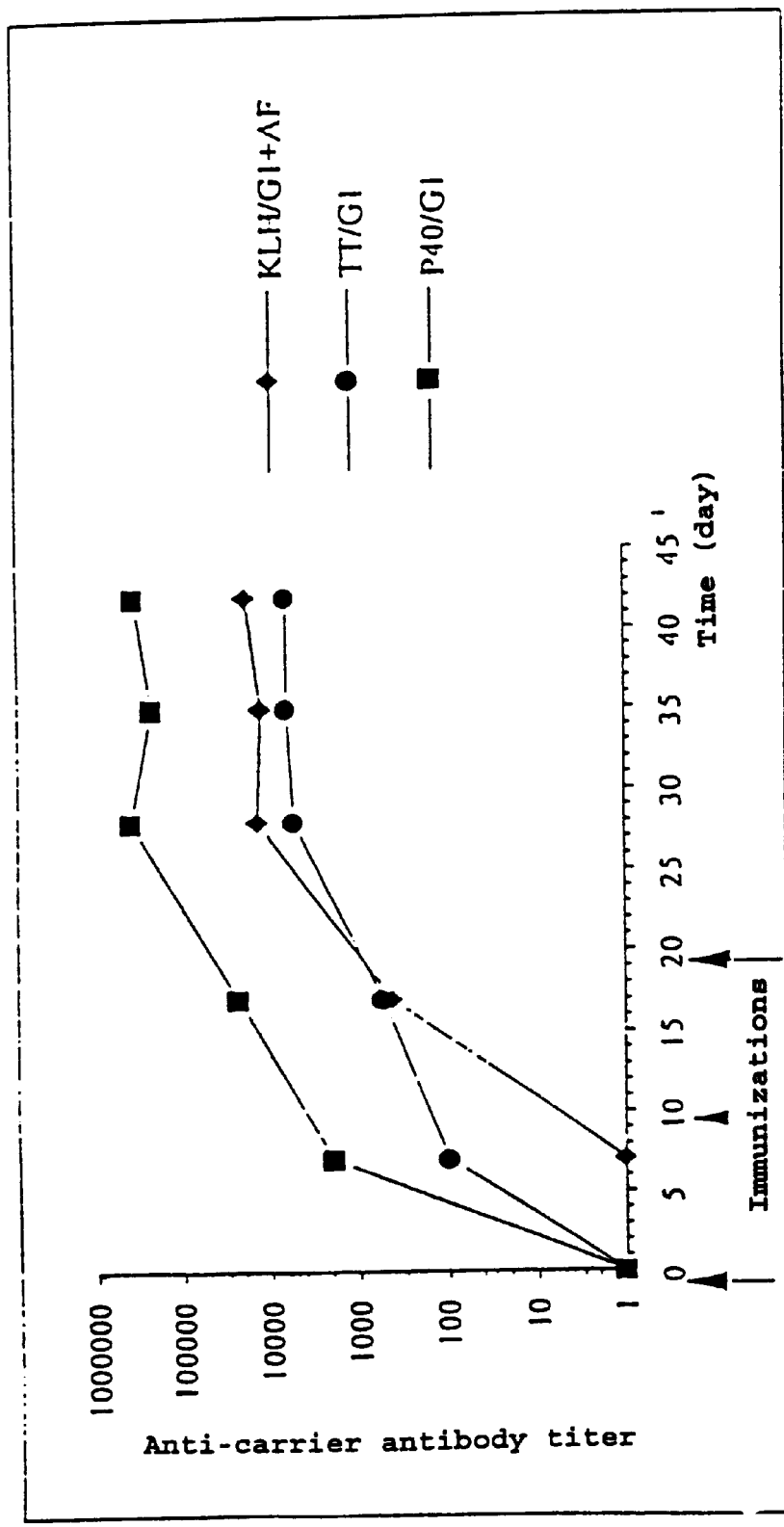
Figure 3:
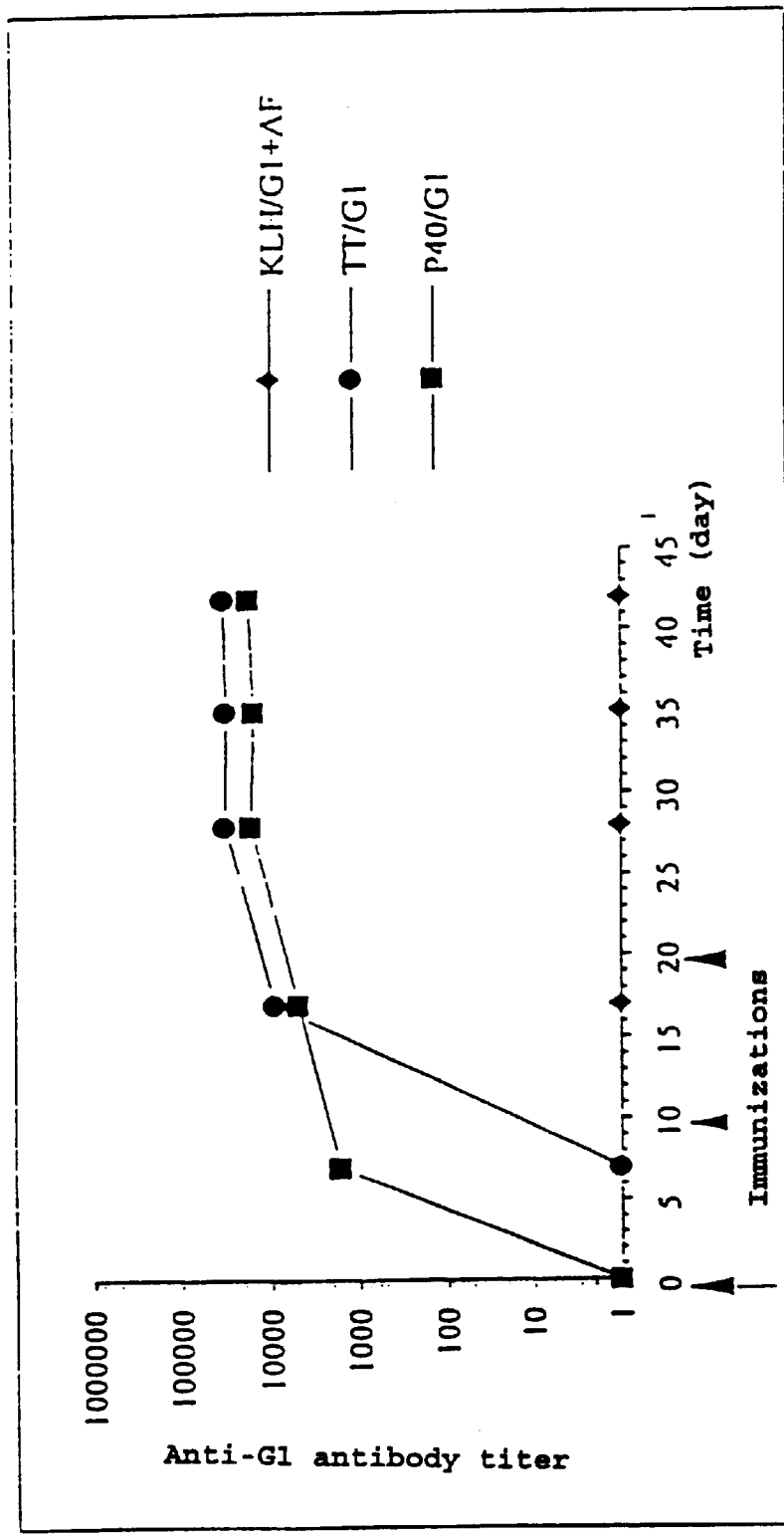
Figure 4:
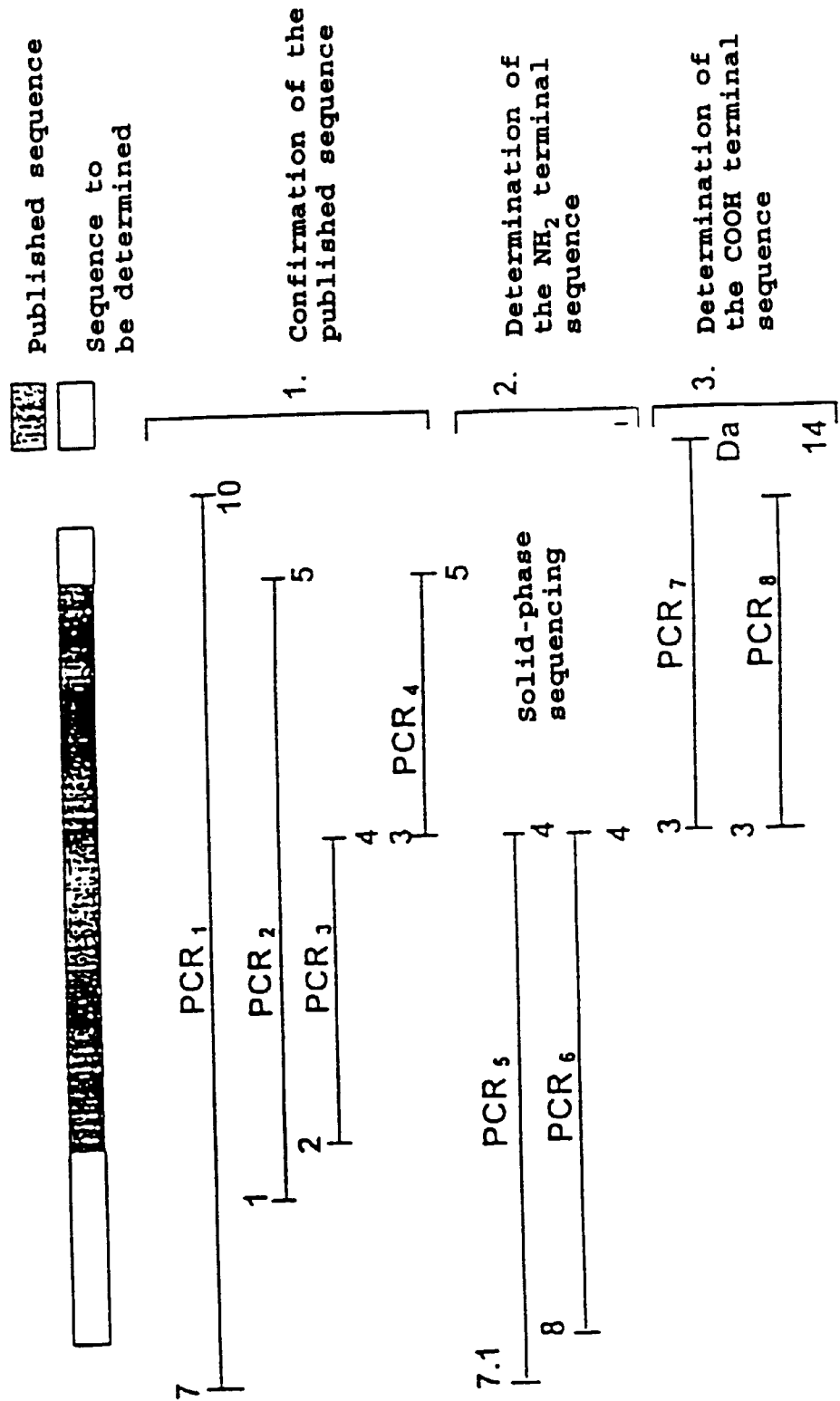

In these examples, reference will be made to the following figures:

FIG. 1: intensity of the immune response induced against G1A in different forms, FIG. 2: kinetics of the immune response induced against G1A presented in different forms, FIG. 3: kinetics of the immune response induced against the carrier alone, FIG. 4: cloning strategy by genetic amplification of p40.

EXAMPLE 1

Synthesis and Purification of $G_1A$

The polypeptide of sequence

Ser-Ile-Cys-Ser-Asn-Asn-Pro-Thr-Cys-Trp-Ala-Ile-Ser-Lys
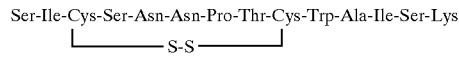

written $G_1A$ is prepared by solid-phase synthesis using Boc chemistry.

Assembly

The assembly of the peptide is carried out by solid-phase peptide synthesis on polystyrene (divinyl-benzene 1%), starting with a Boc-Lys(2-cl-Z)-phenylacetamidophenyl linking agent.

The Boc-benzyl chemical strategy was used with the following deprotection-coupling procedure:

| | | |
|---|---|---|
| 1. | 55% TFA in DCM | (1 × 5 min) |
| 2. | 55% TFA in DCM | (1 × 25 min) |
| 3. | DCM | (2 × 1 min) |
| 4. | Isopropyl alcohol | (1 × 1 min) |
| 5. | DMF | (2 × 1 min) |
| 6. | 10% DIEA in DMF | (2 × 2 min) |
| 7. | Coupling | |
| 8. | DMF | (2 × 1 min) |
| 9. | DCM | (2 × 1 min) |

In each step, 20 ml of solvent are used per gram of peptide resin.

The coupling is carried out in DMF with a preformed hydroxybenzotriazole ester for 30 min. It is verified in each step of the coupling if residual free amine functions are present by the ninhydrin test. If necessary, a double coupling is carried out.

For the synthesis of the $G_1A$ peptide, the following side-chain protection groups were used:

2-chlorobenzyloxycarbonyl for lysine, benzyl for serine and threonine, 4-methylbenzyl for cysteine, formyl for tryptophan.

Before the final deprotection/cleavage step, the formyl group is eliminated by treatment for 30 min with a 25% solution of piperidine in DMF. The peptide resin is washed with DCM and ether, and dried under reduced pressure.

Cleavage

The peptide is cleaved from the resin and completely deprotected by treatment with liquid hydrogen fluoride. 10 ml of hydrogen fluoride per gram of peptide resin are conventionally used at 0° C. for 45 min in the presence of p-cresol and ethanedithiol as a trap. After evaporation of the hydrogen fluoride, the crude reaction mixture is washed with ether, dissolved in TFA, precipitated with ether and dried.

Cyclization and purification

| | |
|---|---|
| Stationary phase: | $C_{18}$ silica, 15–25 µm, 100 Å |
| Mobile phase: | solvent A: water 0.1% TFA |
| | solvent B: acetonitrile/A, 60/40% (v/v) |
| Linear gradient: | 20 to 50% B in 30 min (first purification step) |
| | 15 to 40% B in 30 min (second purification step) |
| Flow rate: | 40 ml/min |
| Detection: | UV (210 nm) |

The crude peptide -obtained after cleavage is purified under the conditions described above (gradient of 20 to 50% B). Fractions having a purity of greater than 70–80% (HPLC) are combined and lyophilized. The peptide is then purified in a mixture of acetonitrile water and DMSO (1 mg/ml) and stirred until the cyclization is complete (4 to 6 days). The progress of the reaction is checked by HPLC. The reaction mixture is finally concentrated on a preparative HPLC column and a gradient of 15 to 40% of B is applied in 30 min so as to purify the peptide.

Generally, after lyophilization, a second purification under the same condition is carried out to attain the degree of purity required.

The purity and the identity of the final product are checked by analytical HPLC, amino-acid analyzis and FAB mass spectrometric analyzis.

In the peptide thus obtained, the serine residue in position thirteen replaces the Cys residue of the natural peptide, thus avoiding heterogeneity in the formation of disulfide bridges, which can be harmful to the immunogenicity.

EXAMPLE 2

Preparation of the Epitope $G_2A\delta Cys$

Gene Construction: Materials and Methods

In an Eppendorf microtube, 300 µg of beads are washed with washing/binding buffer (1M NaCl, 10mM Tris-HCl pH7.5, 1 mM EDTA) before adding 0.2 pmol of biotinylated oligonucleotide; 15 minutes' incubation at ambient temperature for binding. The beads with the immobilized oligonucleotide are rinsed and sedimented. 0.2 pmol of the following 5'-phosphorylated oligonucleotide is added in 60 µl of hybridization/ligation buffer (50mM Tris-HCl pH7.6, 10 mM $MgCl_2$, 1mM ATP, 1 mM 1,4-dithiothreitol [DTT], 5% polyethylene glycol [PEG] 8000-. The hybridization mixture is incubated at 70° C. for 5 min and allowed to come to 37° C. before adding 3 units of T4 DNA ligase (BRL) followed by 15 min incubation at 37° C. The reaction mixture is rinsed before adding 0.2 pmol of the following oligonucleotide. The hybridization/ligation procedure is repeated as many times as a new 5'-phosphorylated complementary oligonucleotide is added. At the end, the DNA duplex immobilized on magnetic beads can be separated from the support by cutting with the appropriate restriction enzymes.

The DNA corresponding to the sequence G2AδCys and to the sequence G2AδCys attached to the linking protein to human serum albumin (BB) written BB-G2AδCys is prepared.

The nucleotide sequence is expressed in E. coli to recover the corresponding proteins.

Expression vector:

pVABBG2AδC is an expression vector of the intracellular type, it contains a promoter of E. coli origin, the tryptophan (Trp) operation, followed by the gene coding for the receptor of human serum albumin BB (P-Å Nygren et al., J. Mol. Recognit., 1988, 1, 60) and finally the gene coding for G2AδC of RSV. The expression of the heterologous gene can be induced in the presence of IAA (3-β-indoleacrylic acid). The fusion product BBG2AδC can be purified by affinity on an HSA-sepharose column, after having liberated the cytoplasmic proteins of E. coli.

Examples of Purification of Proteins Starting from 500 ml of Culture:

The strain E. coli RV 308 (Maurer et al., J. Mol. Biol., 1980, 139, 147) transfected by the plasmid pVABBG2AδC was selected on agar containing ampicillin (100 µg/ml) and tetracycline (8 µg/ml). The strain was inoculated into an Erlenmeyer flask containing 100 ml of TSB culture medium (Tryptic Soy broth, Difco) (30 g/l), supplemented with yeast (Yeast Extract, Difco) (5 g/l), ampicillin (100 µg/ml), tetracycline (8 µg/ml) and tryptophan (100 µg/ml). Incubate at 32° C. for 12 hours with stirring (190 rpm). Transfer the culture into another erlenmeyer flask (5 liters) containing four times the initial volume (400 ml of TSB+yeast+the same antibiotics at the same concentration). When the optical density of the medium (at 550 nm) has reached an O.D. of approximately 1.5, the production of the proceins is induced by adding IAA to the medium to a final concentration of 25 µg/ml. Culturing is stopped after incubation for 5 hours, with stirring (190 rpm) at 32° C. After centrifugation, the bacterial plug is resuspended in a vessel comprising approximately 60 ml of cold TST solution (50 mM TrisHCl, pH 8.0, 200mM NaCl, 0.05% Tween 20, 0.5 mM EDTA).

A standard sonicator probe (VIBRA-CELL, Somics Mat, USA) is introduced into the vessel. Sonication is carried out at a power of 5 for approximately two minutes. The supernatant of the solution after centrifugation is filtered at 0.45 µm, and passed into a column containing approximately 3 ml of HSA-sepharose gel (STÅHL et al., J. Immunol. Meth., 1989, 124, 43).

The purified proteins are analyzed by SDS-PAGE on a Phast System apparatus (PHARMACIA) or on Mini Protean BIORAD. The gels are visualized by Coomassie Blue. The protein BBG2AδC, representing more than 90% purity, corresponds well to the expected size (39.3 Kda) with respect to known molecular weight standards.

The immunotransfer of this protein to a Problott membrane (ABI) allows anti-BB and/or antiprotein G of RSV (ss-group A) to be identified with specific antibodies. The yield of purified soluble proteins starting from the cytoplasm of E. coli is approximately 50 mg/liter of culture.

In a 2-liter fermenter, it is possible to obtain 500 to 800 mg of BBG2AδC proteins per liter of culture under optimum culture conditions.

EXAMPLE 3

Isolation and Purification of the Natural p40 Protein

The process of purification of the P40 protein starting from the biomass of Klebsiella pneumoniae, strain I-145, was developed with one main objective: to develop a process allowing transposition to a large scale and industrial extrapolation. This process successively brings into play the preparation of a fraction enriched in membrane proteins and the purification of the P40 protein by chromatography.

MATERIALS AND METHODS

The biomass of Klebsiella pneumoniae (strain I-145, 40 g of dry cells) is adjusted to pH 2.5 with the aid of pure acetic acid. After addition of ½ volume of a solution comprising 6% cetrimide, 60% ethanol, 1.5 M CaCl2 whose pH is adjusted to 2.5 with acetic acid, the mixture is stirred for 16 hours at ambient temperature.

After centrifugation for 20 min at 15,000 g at 4° C., the proteins of the supernatant are precipitated with ethanol. Two successive precipitations with intermediate centrifugation (10 min, 10,000 g, 4° C.) are carried out: from 20 to 50% then from 50 to 80%.

The plugs obtained after the second precipitation are resuspended in a solution of zwittergent 3–14, 1%.

After stirring for 4 hours at ambient temperature, the pH is adjusted to 6.5 with the aid of 1 N NaOH.

Centrifugation of the mixture for 20 min at 10,000 g at 4° C. allows a fraction enriched in membrane proteins (MP fraction) to be obtained.

The proteins of the MP fraction are dialyzed against a 20 mM Tris/HCl buffer pH 8.0; zwittergent 3–14, 0.1%. The dialyzate is applied to a column containing a support of the strong anion exchanger type (column of diameter=50 mm×H=250 mm, Biorad Macroprep High Q gel) equilibrated in the buffer described above. The P40 protein is eluted by an NaCl concentration of 50 mM in the equilibration buffer.

The fractions containing the P40 are collected and dialyzed against a 20 mM citrate buffer pH 3.0; zwittergent 3–14, 0.1%. The dialyzate is applied to a column containing a support of the strong cation exchanger type (dimensions of the column: diameter=mm×H=160 mm, Biorad Macroprep High S gel) equilibrated in the 20 mM citrate buffer pH 3.0, zwittergent 3–14, 0.1%. The P40 protein is eluted by an NaCl concentration of 0.7 M. The fractions containing the P40 are collected and concentrated by ultrafiltration with the aid of a Minitan Millipore tangential-flow filtration system used with membrane sheets having a 10 kDa cutoff threshold.

RESULTS

The fractions obtained after each chromatographic step are analyzed by SDS-PAGE so as to collect those containing the P40 protein.

The quantities of proteins are measured by the method of Lowry (Table I). The purity and homogeneity of the P40 protein are estimated by SDS-PAGE, in the presence of molecular weight standards.

After the cation exchange chromatography step, the P40 protein is devoid of the major contaminant present in the MP fraction (the protein having an apparent molecular weight of 18 kDa) and has a degree of purity of greater than 95%.

The electrophoretic profile of the P40 reveals several bands. These bands are identified after immunoblot with P40 monoclonal antibodies obtained in mice. The upper major band corresponds to the denatured protein (by treatment at 100° C., 15 min in the presence of SDS), and the lower minor band to the protein in its native form.

P40 is in fact a "heat-modifiable" protein, and we have been able to verify this property with the aid of heating kinetics at 100° C. in the presence of SDS. Without heating, the protein in native form has an a-helix structure which fixes more SDS and thus migrates further toward the anode than the denatured form (denaturation complete after 5 min at 100° C.) which has a β-pleated sheet structure (K.B. KELLER (1978) J. Bacteriol. 134, 1181–1183).

The contamination with lipopolysaccharides (LPS) is estimated by determination by gas-phase chromatography of β-hydroxymyristic acid, the fatty acid marker of LPS of Klebsiella pneumoniae (Table I).

TABLE 1

Table of the quantities of protein and LPS of the fractions obtained for the different steps in the process for the purification of the p40 protein (n.d. = not determined).

| | PROTEINS | YIELD | LPS |
|---|---|---|---|
| BIOMASS | 40 g | — | n.d. |
| MP FRACTION | 900 mg | 2.25% | n.d. |
| FRACTION ENRICHED IN P40 | 400 mg | 1% | 10% |
| P40 PROTEIN | 130 mg | 0.3% | <1% |

This method is used to approximate the content of LPS in the samples from the different purification steps.

The quantity of β-hydroxymyristic acid present in the P40 fraction after cation-exchange chromatography being lower than the quantification threshold of the determination, it is possible to estimate that the quantity of residual LPS is lower than 1%.

EXAMPLE 4

Cloning of the p40 Protein and Expression of BBp40
BACTERIAL STRAINS
  E. coli: RV 308: ATCC 31608 strain (MAURER R., MEYER B. J., PTASCHNE M., J. MOL. BIOL, 1980, 139, 147–161).
  K. pneumoniae: IP 145: C.I.B.P.F-strain
VECTORS
  pRIT 28 (Hultman et al., 1988,7: 629–638): cloning and sequencing vector containing the ampicillin resistance gene, the replication origins of E. coli and of the phage F1 as well as a portion of the lac-z gene of E. coli (β-galactosidose).
  pVABB: gene fusion expression vector.
SOLUTIONS

| * Genetic amplification: | | |
|---|---|---|
| Lysis buffer: | 25 mM Taps pH 9.3 | |
| | 2 mM MgCl2 [sic] | |
| Amplification buffer: | 25 mM Taps pH 9.3 | |
| | 2 mM MgCl2 [sic] | |
| | tween 20 0.1% | |
| | 200 mM dNTP. | |
| * Purification of proteins: | | |
| TST (20X): | Tris base | 0.5 M |
| | HCl | 0.3 M |
| | NaCl | 4 M |
| | Tween 20 | 1% |
| | EDTA | 20 mM |
| Washing buffer: | Tris HCl | 50 mM pH 8.5 |
| | MgCl2 [sic] | 5 mM |
| Denaturation solution: | Gua-HCl | 7.8 M |
| | Tris-HCl | 28 mM pH 8.5 |
| Renaturation solution: | Gua-HCl | 0.5 M |
| | Tris-HCl | 25 mM pH 8.5 |
| | NaCl | 150 mM |
| | Tween 20 | 0.05%. |

MATERIAL AND METHOD
  Synthesis of Oligonucleotides
  The nucleotide primers were determined starting from the published part of the sequence of the OMPA of Klebsiella pneumoniae (LAWRENCE, G. J., et al., Journal of general microbiology, 1991, 137, 1911–1921) of the consensus sequence from the alignment of the sequences of 5 OMPA of enterobacteria (E. coli, S. tryphimurium, S. marcescens, S.

dysenteriae, E. aeroginosae), as well as sequences of peptides obtained by manual sequencing.

The oligonucleotides were synthesized according to the phosphoramidite chemical method on the "Gene Assembler Plus" apparatus from Pharmacia.

Genetic Amplification by PCR of the P40 Gene

The DNA of OMPA of Klebsiella pneumoniae was amplified in the following manner.

A colony of Klebsiella pneumoniae is lysed in 10 μl of lysis buffer by heating to 95° C. for 5 minutes.

1 μl of this solution serves as a source of DNA for the amplification reactions.

These are carried out in 100 μl of amplification buffer (cf. annex), with 5 pmol of each primer and one unit of Taq polymerase enzyme (Perkin Elmer Cetus). Each cycle comprises one denaturation step of 30 seconds at 95° C. followed by a hybridization of the primer to the DNA and an extension of one minute at 72° C. 30 cycles are thus carried out with the aid of a Perkin Elmer Cetus 9000 "Gen Amp PCR" thermocyclizer.

The following PCR are prepared starting from the DNA fragments amplified above.

The amplified DNA fragments are then digested, purified and ligated to the vector pRIT 28.

SEQUENCING

The fragments cloned in this way are sequenced on an Applied Biosystem 373 DNA Sequencer automatic sequencer. The sequencing reactions are carried out with the aid of the "dye Terminator" kit according to the recommendations of the supplier (Applied Biosystem) either on double-stranded DNA obtained after genetic amplification or from maxiprep or on single-stranded DNA from denatured PCR fragments (Hultman et al., Nucleic acids res.; 1989, 17:4937–4946).

EXPRESSION OF THE PROTEIN

The entire P40 gene is cloned in the expression vector pVABB. This vector allows an affinity tail "BB" to be attached to P40; B being the part of the streptococal G protein which ligates serum albumin (Nygren P. A. et al.; Journal mol. Recognit. 1988; 1, 69–74).

The strains of *E. coli* RV308 transformed by the vector pVABBP40 are cultured for one night at 37° C. with stirring, in 100 ml of TSB supplemented with yeast extract, ampicillin (200 μg/ml) tetracycline (8 μg/ml) and tryptophan (100 μg/ml). The next day, a culture of OD=1 for a wavelength of 580 nm is prepared in TSB+yeast extracts+ampi+tetra.

After culturing for 10 minutes, expression of the protein is induced by addition of IAA at (25 μg/ml) to the medium. The culture is centrifuged at 4° C. at 2460 g for 10 minutes.

The plug is taken up with 20 ml of TST 1× pH 7.4, and the solution is then centrifuged at 4° C. at 23,000 g for 30 minutes.

The supernatant is filtered through Sepharose which allows proteins termed soluble to be isolated. The plug is washed with washing buffer and then centrifuged at 23,000 g at 4° C. for 30 minutes. The plug containing the inclusion body is then taken up with 900 μl of a denaturing solution+ 100 μl of 10mM Diothiothreitol and incubated at 37° C. for 2 hours.

The solution is then incubated at ambient temperature for 1 night, with stirring, in 100 ml of renaturation buffer at 2300 g for 1 hour.

The supernatant is filtered through HSA Sepharose.

In the two cases, the immobilized proteins are eluted with 0.5 M acetic acid pH 2.8 and collected in 1 ml fractions.

The fractions collected are then analyzed on SDS-PAGE electrophoresis gel and by Immuno blot.

RESULTS

The cloning of the gene was carried out in three stages according to the strategy presented in FIG. 4.

In a first stage, we confirmed the published part of the sequence with the exception of a T in the place of an A in position 103.

Then we determined the 3'-sequence of the gene and finally the 5'-sequence.

The entire gene was obtained by fusion of the two parts 8/4 and 3/14 and then cloned in the vector pRIT 28. The sequence corresponds to SEQ ID No. 13.

The protein is expressed in the form BBP40.

It is essentially obtained starting from inclusion bodies. For a 200 ml culture, fifteen milligrams of protein are purified.

The electrophoretic profile shows that BBP40, obtained after denaturation, is of high purity. The apparent molecular weight corresponds to the calculated theoretical weight which is 63 kDa.

The Immuno blot characterization shows that the purified protein is indeed recognized by a rabbit anti-P40 serum.

EXAMPLE 5

Coupling of the p40 Protein to the $G_1A$ Peptide p40 (5 mg/ml, 40 mg) is dialyzed against 300 volumes of 0.1 M sodium phosphate buffer pH 7, zwittergent 3–14, 0.1%.

The dialyzate is adjusted to a concentration of 2 mg/ml with the aid of a 0.1 M carbonate buffer pH 9; zwittergent 3–14, 0.1%. Sodium dodecyl sulfate (SDS) is added to obtain a final concentration of 4%.

The $G_1$ peptide (10 mg/10 ml of 0.1 M carbonate buffer pH 9; 0.1% zwittergent 3–14) is added to the p40 solution. The pH is checked (between pH 9 and pH 10).

Add 220 μl of glutaraldehyde (2.5% in water) and stir for 24 hours at 4° C.

Add 5 μl of 0.1 M carbonate buffer pH 9; 0.1% zwittergent 3–14; check the pH (between pH 9 and pH 10); stir for 72 hours at 4° C.

Add 220 μl of glutaraldehyde (2.5% in water), check the pH, stir for 24 hours at +4° C.

The reaction is stopped by addition of 100 μl of 1 M lysine. The solution is dialyzed for 24 hours at 4° C.

The SDS is eliminated by double KCl precipitation.

The solution containing the p40 conjugate is frozen and used as such or lyophylized.

EXAMPLE 6

Activity

MATERIAL AND METHODS

C57BL/6 mice (N=5) are immunized on day 0, day 10 and day 20 by the subcutaneous route with 10 μg of G1, optionally coupled to a carrier, in the presence or absence of an adjuvant. The serum is collected and tested by ELISA. The anti-G1 or anti-carrier Igs are isolated on a BSA-G1 support and on a "carrier" support (KLH or TT or P40). The Igs are visualized with the aid of an anti-Ig rabbit peroxidase conjugate. The optical density is read at 450 nm and the anti-G1 antibody titer is given by the reciprocal of the last dilution giving twice the background noise. The results represent the mean± standard deviation of the titers of 5 mice.

RESULTS

Induction of an immune response against G1A

The mice are immunized with G1A in different forms according to an identical immunization scheme. The antibody responses induced by the different forms of G1A are compared 28 days after the start of the experiment.

The synthetic G1A peptide administered pure does not induce any immune response even if it is coadministered with Freund's adjuvant. Presented with the carrier KLH, G1A induces a weak response which is significantly increased by the coadministration of Freund's adjuvant (FA). Presented with p40, G1A induces a greater response than that obtained in the conventional KLH/G1+AF, p40 immunization scheme to "self-adjuvant carrier" properties.

The results are presented in FIG. 1.

Kinetics of the immune response to G1A

The mice are immunized with G1A in different forms according to an identical immunization scheme. The antibody responses induced by the different forms of G1A are compared at the times: 7, 17, 28, 35, 42 days after the start of the experiment.

The anti-G1A response is significantly higher and more rapid when the mice are immunized with p40/G1A than the more conventional TT/G1A and KLH/G1A+AF immunizations. A single injection of p40/G1A allows an anti-G1A antibody titer of 1000 to be obtained in 7 days. This titer is obtained with TT/G1A or KLH/G1A+AF in 28 days. The maximum response (titer=1/380 000), obtained after three injections, in 28 days is approximately 30 times greater than that obtained with KLH/G1A+AF and 70 times greater than that obtained with TT/G1A. The anti-G1A antibody titer holds steady without weakening until day 42.

The results are presented in FIG. 2.

Kinetics of the Immune Response to the Carrier

The mice are immunized with G1A coupled to a carrier according to an identical immunization scheme. The antibody responses induced by the different carriers are compared at the times 7, 17, 28, 35 and 42 days after the start of the experiment.

The anti-p40 response (titer close to 10,000) is higher than the anti-KLH response but not significantly different to the anti-TT response.

The results are presented in FIG. 3.

CONCLUSION

The chemical coupling of the G1A peptide to the p40 protein allowed a significantly more important and more rapid anti-G1A response to be induced than that provoked by the KLH/G1A+AF or TT/G1A reference models. Coupling of the G1B peptide ought to induce similar responses.

EXAMPLE 7

Evaluation of the Protective Potential of Peptides and of Recombinant Proteins of Glycoprotein G of Respiratory Syncytial Virus (RSV) Subgroup A Coupled to p40 Carrier Protein BALB/c mice were immunized with the following different preparations:

1) G1A synthetic peptide coupled to KLH (keyhole limpet hemocyanin)=KLH.G1A.
2) G1A synthetic peptide coupled to p40 carrier protein=p40. G1A.
3) p40 control alone.
4) Recombinant protein produced in *E. coli*: BBG2AδC coupled to p40 carrier protein=p40. BBG2AδC.
5) G1A synthetic peptide coupled to tetanus toxin (TT) carrier protein=TT.GLA.
6) TT control alone.
7) BB control alone.
8) Long RSV control (subgroup A).

The mice received 3 intramuscular doses (200 μg/mouse) with aluminum hydroxide as adjuvant (used currently in man). The results of the protection tests as well as the immunological profile of the sera are found in Table 2.

The following preparations confer complete protection following challenge with long RSV (strain A): p40. G1A, p40. BBG2AδC, with respect to TT.G1A which also confers very good protection comparable to the peptide KLH.G1A. In the ELISA test, they all recognize RSV antigen with the highest titer for p40. G1A=1/12800.

As for the neutralization test, none of the preparations possess any neutralizing activity in vitro.

TABLE 2

Protection conferred and immunological profile of the sera after challenge with long RSV (A) following immunization of BALB/c mice with different recombinant proteins. (3–4 weeks after 3 doses i.m. with Aluminum hydroxide)

| Recombinant peptides and proteins | Protection DICT$_{50}$ log10/g lungs challenge with long RSV (1.5 × 10$^5$/mouse) (subgroup A) | | | | Elisa titer versus long RSV | Neutralization log 2/25 μl |
|---|---|---|---|---|---|---|
| | 5–6 days | | 7–8 days | | | |
| KLH.G1A | 2.45 | ≦2.0 ± 0.4 | 2.45 | ≦2.0 ± 0.4 | 4000 | <3.0 |
| (100 to 157 μg) | 2.45 | p < 0.001 | 2.15 | p < 0.001 | | |
| | <1.7 | | <1.7 | | | |
| | <1.7 | | <1.7 | | | |
| | <1.7 | | <1.7 | | | |
| P40.G1A | <1.7 | <1.7 ± 0 | <1.7 | <1.7 ± 0 | 12800 | <3.0 |
| (200 μg) | <1.7 | p < 0.001 | <1.7 | p < 0.001 | | |
| | <1.7 | | <1.7 | | | |
| | <1.7 | | <1.7 | | | |

TABLE 2-continued

Protection conferred and immunological profile of the sera after challenge with long RSV (A) following immunization of BALB/c mice with different recombinant proteins. (3–4 weeks after 3 doses i.m. with Aluminum hydroxide)

| Recombinant peptides and proteins | Protection DICT$_{50}$ log10/g lungs challenge with long RSV (1.5 × 10$^5$/mouse) (subgroup A) 5–6 days | | 7–8 days | | Elisa titer versus long RSV | Neutralization log 2/25 μl |
|---|---|---|---|---|---|---|
| P40 controls (200 μg) | 4.7<br>4.45<br>4.45<br>4.45 | 4.5 ± 0.1<br>p < 0.001 | 4.7<br>4.45<br>4.45<br>4.45 | 4.5 ± 0.1<br>p < 0.001 | 300 | <3.0 |
| P40.BBG2AδC (200 μg) | <1.7<br><1.7<br><1.7<br><1.7<br><1.7 | <1.7 ± 0<br>p < 0.001 | <1.7<br><1.7<br><1.7<br><1.7<br><1.7 | <1.7 ± 0<br>p < 0.001 | 1700 | <3.0 |
| TT.G1A (200 μg) | <1.7<br><1.7<br><1.7<br><1.7<br>2.45 | <1.9 ± 0.3<br>p < 0.001 | <1.7<br><1.7<br><1.7<br><1.7<br>2.45 | <1.9 ± 0.3<br>p < 0.001 | 7200 | <3.0 |
| TT controls (200 μg) | 4.45<br>4.2<br>4.2<br>4.45<br>3.7 | 4.2 ± 0.3<br>p = 0.022 | 4.7<br>4.2<br>4.2<br>4.45<br>3.7 | 4.2 ± 0.4<br>p = 0.053 | 250 | <3.0 |
| BB controls (200 μg) | 2.95<br>4.2<br>3.95<br>3.7<br>3.7 | 3.7 ± 0.5<br>p = 0.853 | 2.95<br>4.2<br>4.2<br>3.7<br>3.7 | 3.8 ± 0.5<br>p = 0.760 | 150 | <3.0 |
| Long RSV controls | <1.7<br><1.7<br><1.7<br><1.7<br><1.7 | <1.7 ± 0<br>p = 0.001 | <1.7<br><1.7<br><1.7<br><1.7<br><1.7 | <1.7 ± 0<br>p = 0.001 | 76800 | 6.6 |
| Controls, nonimmunized, challenged | 3.95<br>3.95<br>3.7<br>3.45<br>3.95<br>3.45 | 3.7 ± 0.2 | 3.95<br>4.2<br>3.7<br>3.45<br>3.95<br>3.7 | 3.8 ± 0.3 | 150 | <3.0 |
| Controls, nonimmunized, unchallenged | No virus | | No virus | | 150 | <3.0 |

EXAMPLE 8

Evaluation of the protective potential of peptides of gloycoprotection of respiratory syncytial virus (RSV) subgroup A and subgroup B coupled to KLH. Protection against a challenge carried out with the two subgroups of RSV.

BALB/c mice were immunized with the following different preparations:

1. C1A synthetic pepitde coupled to KLH (keyhole limpet hemocyanin)=KLH-G1A
2. G1B synthetic peptide coupled to KLH (keyhole limpet hemocyanin)=KLH-G1B. The G1B peptide corresponds to the sequence G (174–187)δCys of the subgroup B whose sequence is:

Ser-Ile-Cys-Gly-Asn-Asn-Gln-Leu-Cys-Lys-Ser-Ile-Ser-Lys
     |————— S-S ——————|

3. KLH control
4. Long RSV control (subgroup A)
5. 8/60 VRS control (subgroup B)

The mice recived 3 intramuscular doses (200 μg/mouse) with freud's adjuvant. The results of the protection tests as well as the immunological profile of the sera are found in Table 3.

The preparation KLH-G1A allows complete protection against RSV subgroup A but not against RSV subgroup B. On the contrary, the preparation KLH-G1B allows complete protection against RSV subgroup B but not against RSV subgroup A. The ELISA test reflects the same situation.

TABLE 3

Protection conferred and immunological profile of the sera after challenge with long RS (subgroup A) or with RS [sic] 8/60 (subgroup B) following immunization of BALB/c mice with the peptides G1A and G1B.

| | PROTECTION DICT$_{10}$ log 10/g lungs | | ELISA titer | |
|---|---|---|---|---|
| Peptides coupled to KLH | Challenge Long RSV (subgroup A) 1.5 × 10$^5$/s (50 µl) | Challenge 8/60 RSV (subgroup B) 0.6 × 10$^5$/s (50/µl) | Versus long RSV (A) | Versus 8/60 RSV (B) |
| G1A | ≦1.8 ± 0.3 n = 11 p < 0.001 | 3.3 ± 0.5 n = 10 p = 0.237 | 29866 | 266 |
| G1B | 3.8 ± 0.8 n = 7 p = 0.517 | ≦2.1 ± 0.5 n = 8 p < 0.001 | ≦100 | 7200 |
| KLH control | 3.7 ± 0.3 n = 11 p = 0.01 | 3.4 ± 0.3 n = 10 p = 0.6 | ≦200 | 133 |
| VRS (A) control | ≦1.7 ± 0 n = 11 p < 0.001 | ≦1.7 ± 0 n = 11 p < 0.001 | ≦68266 | 51200 |
| VRS (B) control | ≦1.7 ± 0 n = 10 p < 0.001 | ≦1.7 ± 0 n = 10 p < 0.001 | ≦76800 | 68266 |

EXAMPLE 9

Veterinary Application

Evaluation of the protective potential of G1vΔC peptide derived from protein G of the bovine strain of Respiratory Syncytial Virus (RSV) Lerch et al., 1990, J. Virol. 64:5559 coupled to KLH carrier protein. 174 187

Ser Thr Cys Glu Gly Asn Leu Ala Cys Leu Ser Leu Ser His having a disulfide bridge in position 176–182.

The peptide prepared by solid-phase synthesis using Boc chemistry is coupled to KLH using glutaraldehyde (Schaaper et al., Mol. Immunol. (1989) 26:81–85).

Two calves were immunized by the intramuscular route with 500 $\mu$g of GlvΔC-KLH with incomplete Freund's adjuvant 3 times at intervals of 3 weeks. One calf was immunized with KLH without GlVAC peptide and with an incomplete Freund's adjuvant.

The animals are challenged with the Snook strain, 21 days after the last inoculation, by the intranasal and intratracheal route each with lml of virus titrating at 2×105/ml.

The virus titrated on calf kidney cells according to the plaque method is determined in nasopharyngeal washings 3 and 2 days respectively after challenge and 7 days in the lungs of the sacrificed animals.

CIRCULATING ANTIBODY RESPONSE:

Calf 3432 (KLH + FIA):

| Date | Treatment | log10 ELISA titer: Peptide + KLH | Peptide | KLH | BRSV (Snook) |
|---|---|---|---|---|---|
| 23/11 | Day 0 vaccination | <1.0 | <1.0 | <1.0 | <1.5 |
| 14/12 | Day 21 vaccination | <1.0 | <1.0 | 3.0 | <1.5 |
| 04/01 | Day 42 vaccination | <1.0 | <1.0 | 4.7 | <1.5 |
| 01/02 | Day 70 VRS IN/IT | <1.0 | <1.0 | 5.7 | <1.5 |
| 08/02 | Day 77 sacrifice | 1.5 | <1.0 | 4.8 | <1.5 |

Calf 3440 (Peptide - KLH + FIA)

| Date | Treatment | log10 ELISA titer: Peptide + KLH | Peptide | KLH | BRSV (Snook) |
|---|---|---|---|---|---|
| 23/11 | Day 0 vaccination | <1.0 | <1.0 | <1.0 | <1.5 |
| 14/12 | Day 21 vaccination | 1.6 | <1.0 | <1.0 | <1.5 |
| 04/01 | Day 42 vaccination | 3.8 | 2.6 | 1.7 | 1.9 |
| 01/02 | Day 70 VRS IN/IT | 2.7 | 2.8 | 2.6 | 3.7 |
| 08/02 | Day 77 sacrifice | 4.1 | 2.6 | 1.7 | 3.1 |

Calves to which 500 g of G1vΔC-KLHen incomplete Freund's adjuvant was administered on three occasions at 3 week intervals.

RESPONSE TO THE VIRUS CHALLENGE

| Calves | Vaccination | Nasopharyngeal widening: No. of days | Nasopharyngeal widening: max. titer | Day 7 pulmonary virus: LBA titer (pfu/ml) | Day 7 pulmonary virus: Lung homog. | % pneumoniae |
|---|---|---|---|---|---|---|
| 3432 | KLH + FIA | 3 | $5.1 \times 10^3$ | $1.4 \times 10^2$ | 3/3 | 12 |
| 3440 | peptide – KLH + FIA | 2 | $5.5 \times 10^2$ | <0.7 | 0/3 | <1 |

REPLACEMENT SHEET (RULE 26 )

CIRCULATING ANTIBODY RESPONSE

| Calves | Vaccination | log10 ELISA titer (Snook BRSV): Day 0 | Day 24 | Day 42 | Day 68 | Day 75 |
|---|---|---|---|---|---|---|
| 4138 | KLH + FIA | <1.5 | <1.5 | <1.5 | <1.5 | 2.4 |
| 4140 | *Peptide – KLH + FIA | <1.5 | <1.5 | 3.0 | 2.5≈ | 2.9 |

*Calf to which 500 $\mu$g of BP 4006 – KLH in incomplete Freund's adjuvant was administered on three occasions at three week intervals.

RESPONSE TO THE VIRUS CHALLENGE

| Calves | Vaccination | Nasopharyngeal widening No. of days | Nasopharyngeal widening max. titer | Day 7 pulmonary virus LBA titer (pfu/ml) | Day 7 pulmonary virus Lung homog. | % pneumoniae |
|---|---|---|---|---|---|---|
| 4138 | KLH + FIA | 5 | $4 \times 10^1$ | $6.5 \times 10^2$ | 2/3 | 27 |
| 4140 | peptide – KLH + FIA | 4 | $2 \times 10^3$ | $7.0 \times 10^1$ | 3/3 | 2 |

What is claimed is:

1. Polypeptide which can be used as an immunogenic element carried by the peptide sequence between the amino acid residues 130 and 230 of the sequence of the G protein of human respiratory syncytial virus of subgroup A and of subgroup B, or of bovine respiratory syncytial virus, selected from the group consisting of peptides with sequences SEQ ID No. 3, SEQ ID No. 4, SEQ ID No. 8, SEQ ID No. 14, SEQ ID No. 16, SEQ ID No. 18, SEQ ID No. 30 to SEQ ID No. 36, SEQ ID No. 44 to SEQ ID No. 50, SEQ ID No. 52, SEQ ID No. 61 to SEQ ID No. 66G, SEQ ID No. 68 AND SEQ ID No. 73.

2. Polypeptide according to claim 1, characterized in that it additionally comprises at least one cysteine residue in the N-terminal or C-terminal position.

* * * * *

UNITED STATES PATENT AND TRADEMARK OFFICE
CERTIFICATE OF CORRECTION

PATENT NO.  : 6,113,911
DATED       : Sept. 5, 2000
INVENTOR(S) : H. Binz, T. N'Guyen Ngoc, T. Baussant, M. Trudel It is certified that error appears in the above-indentified patent and that said Letters Patent is hereby corrected as shown below:

Column 2, line 49:  At the end of the line, insert:
    -- 1 (or G2A). --.

Column 7, line 2:  Insert:  -- General Conditions of
    Purification by HPLC --.

Column 8, line 23:  "proceins" should read:
    -- proteins --.

Column 9, line 29:  "diameter = mm x H" should read:
    -- diameter = 25mm x H --.

Column 9, line 59:  "a-helix" should read:
    -- α-helix --.  Page 16, line 25

Column 12, line 40:  "Add 5µl" should read:
    -- Add 5ml --.

Column 14, line 28:  "TT.GLA" should read:
    -- TT.G1A --.

UNITED STATES PATENT AND TRADEMARK OFFICE
CERTIFICATE OF CORRECTION

PATENT NO. : 6,113,911
DATED : Sept. 5, 2000
INVENTOR(S) : H. Binz, T. N'Guyen Ngoc, T. Baussant, M. Trudel It is certified that error appears in the above-indentified patent and that said Letters Patent is hereby corrected as shown below:

Column 15, line 54: "gloycoprotection" should read
-- glycoprotein G --.

Column 16, line 58: "recived" should read:
-- received --.

Column 16, line 59: "freud's" should read:
-- Freund's --.

Column 84, line 47: "SEQ ID No. 66G" should read:
-- SEQ ID No. 66 --.

Signed and Sealed this

Twenty-second Day of May, 2001

Attest:

NICHOLAS P. GODICI

Attesting Officer     Acting Director of the United States Patent and Trademark Office